United States Patent
Firminger et al.

(10) Patent No.: US 8,265,945 B2
(45) Date of Patent: *Sep. 11, 2012

(54) TEMPLATE MODIFICATION BASED ON DEVIATION FROM COMPLIANT EXECUTION OF THE TEMPLATE

(75) Inventors: Shawn P. Firminger, Redmond, WA (US); Jason Garms, Redmond, WA (US); Roderick A. Hyde, Redmond, WA (US); Edward K. Y. Jung, Bellevue, WA (US); Chris D. Karkanias, Sammamish, WA (US); Eric C. Leuthardt, St. Louis, MO (US); Royce A. Levien, Lexington, MA (US); Richard T. Lord, Tacoma, WA (US); Robert W. Lord, Seattle, WA (US); Mark A. Malamud, Seattle, WA (US); John D. Rinaldo, Jr., Bellevue, WA (US); Clarence T. Tegreene, Bellevue, WA (US); Kristin M. Tolle, Redmond, WA (US); Lowell L. Wood, Jr., Bellevue, WA (US)

(73) Assignee: The Invention Science Fund I, LLC

( * ) Notice: Subject to any disclaimer, the term of this patent is extended or adjusted under 35 U.S.C. 154(b) by 302 days.

This patent is subject to a terminal disclaimer.

(21) Appl. No.: 12/655,250

(22) Filed: Dec. 23, 2009

(65) Prior Publication Data

US 2011/0054940 A1    Mar. 3, 2011

Related U.S. Application Data

(63) Continuation-in-part of application No. 12/584,489, filed on Sep. 3, 2009, and a continuation-in-part of application No. 12/584,653, filed on Sep. 8, 2009, and a continuation-in-part of application No. 12/587,018, filed on Sep. 29, 2009, and a continuation-in-part of (Continued)

(51) Int. Cl.
    *G06Q 10/00* (2012.01)
(52) U.S. Cl. .................................................. 705/1.1
(58) Field of Classification Search .................. None
    See application file for complete search history.

(56) References Cited

U.S. PATENT DOCUMENTS 4,853,854 A    8/1989   Behar et al.
(Continued)

OTHER PUBLICATIONS

Chen, Jason; "You Can Soon Track Your Heart Rate with Your iPhone"; Gizmodo; Bearing a date of Oct. 9, 2009; p. 1; Creative Commons License; located at: http://gizmodo.com/5378340/you-can-soon-track-your-heart-rate-with-your-iphone; printed on Oct. 29, 2009.

(Continued)

*Primary Examiner* — Jonathan Ouellette

(57) ABSTRACT

A computationally implemented method includes, but is not limited to: determining whether a plurality of end users deviated from compliantly executing a template designed to facilitate the plurality of end users in achieving one or more target outcomes when one or more emulatable aspects included in the template are emulated by the plurality of end users, the one or more emulatable aspects being based on one or more relevant reported aspects of one or more source users that were deemed to have been relevant to achieving the one or more target outcomes; and modifying the template based, at least in part, on determining that the plurality of end users deviated from compliantly executing the template In addition to the foregoing, other method aspects are described in the claims, drawings, and text forming a part of the present disclosure.

45 Claims, 14 Drawing Sheets

Related U.S. Application Data application No. 12/587,127, filed on Sep. 30, 2009, and a continuation-in-part of application No. 12/590,027, filed on Oct. 29, 2009, and a continuation-in-part of application No. 12/590,039, filed on Oct. 30, 2009, and a continuation-in-part of application No. 12/590,600, filed on Nov. 10, 2009, and a continuation-in-part of application No. 12/590,841, filed on Nov. 12, 2009, and a continuation-in-part of application No. 12/592,075, filed on Nov. 17, 2009, and a continuation-in-part of application No. 12/592,161, filed on Nov. 18, 2009, and a continuation-in-part of application No. 12/592,544, filed on Nov. 24, 2009, and a continuation-in-part of application No. 12/592,548, filed on Nov. 25, 2009, and a continuation-in-part of application No. 12/592,944, filed on Dec. 3, 2009, and a continuation-in-part of application No. 12/592,946, filed on Dec. 4, 2009, and a continuation-in-part of application No. 12/653,117, filed on Dec. 7, 2009, and a continuation-in-part of application No. 12/653,180, filed on Dec. 8, 2009, and a continuation-in-part of application No. 12/653,387, filed on Dec. 10, 2009, and a continuation-in-part of application No. 12/653,386, filed on Dec. 11, 2009, and a continuation-in-part of application No. 12/653,972, filed on Dec. 17, 2009, and a continuation-in-part of application No. 12/655,075, filed on Dec. 21, 2009.

(56) References Cited

U.S. PATENT DOCUMENTS

| | | | |
|---|---|---|---|
| 5,961,446 A | 10/1999 | Beller et al. | |
| 6,338,044 B1 | 1/2002 | Cook et al. | |
| 6,353,447 B1 | 3/2002 | Truluck et al. | |
| 6,842,604 B1 | 1/2005 | Cook et al. | |
| 7,587,368 B2 | 9/2009 | Felsher | |
| 7,668,735 B2 | 2/2010 | Grace et al. | |
| 7,702,685 B2 | 4/2010 | Shrufi et al. | |
| 7,860,852 B2 | 12/2010 | Brunner et al. | |
| 7,908,182 B1 | 3/2011 | Gupta | |
| 7,959,567 B2 | 6/2011 | Stivoric et al. | |
| 8,005,906 B2 | 8/2011 | Hayashi et al. | |
| 2002/0107707 A1 | 8/2002 | Naparstek et al. | |
| 2004/0015337 A1* | 1/2004 | Thomas et al. | 703/11 |
| 2005/0197553 A1 | 9/2005 | Cooper | |
| 2005/0216300 A1 | 9/2005 | Appelman et al. | |
| 2006/0036619 A1* | 2/2006 | Fuerst et al. | 707/100 |
| 2007/0088576 A1 | 4/2007 | de Beus et al. | |
| 2008/0091471 A1 | 4/2008 | Michon et al. | |
| 2008/0288425 A1* | 11/2008 | Posse et al. | 706/12 |
| 2008/0294012 A1* | 11/2008 | Kurtz et al. | 600/300 |
| 2009/0044113 A1 | 2/2009 | Jones et al. | |
| 2009/0070679 A1 | 3/2009 | Shen et al. | |
| 2009/0075242 A1 | 3/2009 | Schwarzberg et al. | |
| 2009/0076335 A1 | 3/2009 | Schwarzberg et al. | |
| 2009/0100469 A1 | 4/2009 | Conradt et al. | |
| 2009/0176526 A1* | 7/2009 | Altman | 455/556.1 |
| 2009/0258710 A1* | 10/2009 | Quatrochi et al. | 463/43 |
| 2009/0271247 A1 | 10/2009 | Karelin et al. | |
| 2009/0292814 A1 | 11/2009 | Ting et al. | |
| 2009/0299990 A1* | 12/2009 | Setlur et al. | 707/5 |
| 2009/0313041 A1* | 12/2009 | Eder | 705/2 |
| 2009/0319288 A1 | 12/2009 | Slaney et al. | |
| 2009/0326981 A1* | 12/2009 | Karkanias et al. | 705/3 |
| 2010/0063993 A1* | 3/2010 | Higgins et al. | 709/203 |
| 2010/0114788 A1 | 5/2010 | White et al. | |
| 2010/0268830 A1 | 10/2010 | McKee et al. | |
| 2010/0281364 A1* | 11/2010 | Sidman | 715/713 |
| 2010/0293247 A1 | 11/2010 | McKee et al. | |
| 2010/0305806 A1* | 12/2010 | Hawley | 701/33 |
| 2011/0022602 A1 | 1/2011 | Luo et al. | |
| 2011/0179161 A1 | 7/2011 | Guy et al. | |
| 2011/0185020 A1 | 7/2011 | Ramamurthy et al. | |
| 2011/0252101 A1* | 10/2011 | Davis et al. | 709/206 |

OTHER PUBLICATIONS

"ErgoPR Software: Ergo Pro Computer Fatigue Software reminds you when to stretch and shows you how"; Bioexsystems.com; Bearing dates of 1995-2009; pp. 1-3; BioEx Systems Inc.; located at: http://www.bioexsystems.com/ExerciseBreak.htm; printed on Dec. 17, 2009.

"Exercise Pro Software Active Care Version 5"; Bioexsystems.com; Bearing dates of 1995-2009; pp. 1-4; BioEx Systems Inc.; located at: http://www.bioexsystems.com/ActiveCare.htm; printed on Dec. 17, 2009.

"Fitbit"; Bearing a date of 2009; pp. 1-2; Fitbit, Inc.; located at: http://www.fitbit.com; printed on Oct. 29, 2009.

"FREE Exercise Programs—Workout Routines & Weight Loss Diet Plans"; Freetrainers.com; Bearing dates of 2000-2008; pp. 1-2; located at: http://www.freetrainers.com/FT/jsp/index.jsp; printed on Sep. 2, 2009.

Guez, Tomer; "Weight Loss Software, Food Diary, Exercise Tracker, and Medical Diary: 'The Food and Exercise Diary Software Version 6.0'"; Weightlosssoftware.com; Bearing a date of Sep. 2009; pp. 1-17; TG Enterprises, Inc.; located at: http://www.weightloss-software.com/?ti=l35&wn=2; printed on Dec. 17, 2009.

"Nutritionmaker Focus: Nutrition Software Motivate—Analyze—Instruct"; Bioexsystems.com; Bearing dates of 1995-2009; pp. 1-4; BioEx Systems Inc.; located at: http://www.bioexsystems.com/NutritionMakerChiro.htm; printed on Dec. 17, 2009.

"Nutrition Tracking Software is Critical for Learning about Foods and Planning Meals"; NutriCoach.net; Bearing a date of Mar. 29, 2006; 6 Total Pages; located at: http://www.nutricoach.net/diet_software.html; printed on Dec. 17, 2009.

"VHI PC—Kits Desktop Edition"; VHIKits.com; pp. 1-2; located at: http://www.vhikits.com/products/software/PCKitsDesktop.aspx; printed on Dec. 17, 2009.

Wilson, Mark; "Philips DirectLife Turns Exercise Into a Status Bar"; Gizmodo; Bearing a date of Oct. 21, 2009; pp. 1-2; Creative Commons License; located at: http://gizmodo.com/5386577/philips-directlife-turns-exercise-into-a-status-bar; printed on Oct. 29, 2009.

"Your Personalized Development Plan"; Central Michigan University; Bearing a date of 2004; p. 1; located at: http://www.chsbs.cmich.edu/leader_model/dplanintro.htm; printed on Sep. 2, 2009.

Agger, Michael;"Every Day We Write the Book: What would happen if Facebook made its data available for research?"; Slate; bearing date of Nov. 30, 2010; printed on Dec. 10, 2010; pp. 1-3; located at: http://www.slate.com/formatdynamics/CleanPrintProxy.aspx?1292008532368.

"Self-tracking links to get you started"; The Quantified Self: self knowledge through numbers; printed on Dec. 10, 2010; pp. 1-5; located at: http://quantifiedself.com/self-tracking-links-to-get-you-started/.

U.S. Appl. No. 12/655,582, Firminger et al.
U.S. Appl. No. 12/655,581, Firminger et al.
U.S. Appl. No. 12/655,365, Firminger et al.
U.S. Appl. No. 12/655,075, Firminger et al.
U.S. Appl. No. 12/653,972, Firminger et al.
U.S. Appl. No. 12/653,387, Firminger et al.
U.S. Appl. No. 12/653,386, Firminger et al.
U.S. Appl. No. 12/653,180, Firminger et al.
U.S. Appl. No. 12/653,117, Firminger et al.
U.S. Appl. No. 12/592,946, Firminger et al.
U.S. Appl. No. 12/592,944, Firminger et al.
U.S. Appl. No. 12/592,548, Firminger et al.
U.S. Appl. No. 12/592,544, Firminger et al.
U.S. Appl. No. 12/592,161, Firminger et al.
U.S. Appl. No. 12/592,075, Firminger et al.
U.S. Appl. No. 12/590,841, Firminger et al.
U.S. Appl. No. 12/590,600, Firminger et al.

U.S. Appl. No. 12/590,039, Firminger et al.
U.S. Appl. No. 12/590,027, Firminger et al.
U.S. Appl. No. 12/587,127, Firminger et al.
U.S. Appl. No. 12/587,018, Firminger et al.
U.S. Appl. No. 12/584,653, Firminger et al.
U.S. Appl. No. 12/584,489, Firminger et al.
Diaz, Jesus; "One Day, This Will Be Remembered as the First Real Tricorder"; gizmodo.com; bearing a date of Nov. 12, 2009; pp. 1-2; located at http://gizmodo.com/5403126/one-day-this-will-be-remembered-as-the . . . ; printed on Nov. 25, 2009.

Gross, Daniel; "A Jewish Mother in Your Cell Phone"; Slate; bearing a date of Nov. 10, 2009; pp. 1-3; located at http://www.slate.com/formatdynamics/CleanPrintProxy.aspx?125919 . . . ; printed on Nov. 25, 2009.

Gaonkar, Shravan, et al.; "Micro-Blog: Sharing and Querying Content Through Mobile Phones and Social Participation"; MobiSys '08; Jun. 17-20, 2008; pp. 174-186; ACM.

* cited by examiner

104 Template Modifying Module

230 Emulatable Aspect Modifying Module

232 Emulatable Aspect Revising Module

234 Emulatable Aspect Replacing Module

236 Emulatable Aspect Deleting Module

238 Emulatable Aspect Adding Module

240 Relationship Defining Module

242 Relationship Modifying Module

243 Reported Aspect Analyzing Module

244 Emulatable Aspect Developing Module

246 Mean Value Emulatable Aspect Developing Module

248 Average Value Emulatable Aspect Developing Module

FIG. 2b

TEMPLATE MODIFICATION BASED ON DEVIATION FROM COMPLIANT EXECUTION OF THE TEMPLATE

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

RELATED APPLICATIONS

For purposes of the USPTO extra-statutory requirements, the present application constitutes a continuation-in-part of U.S. patent application Ser. No. 12/584,489, entitled PERSONALIZED PLAN DEVELOPMENT, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 3 Sep. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/584,653, entitled PERSONALIZED PLAN DEVELOPMENT, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 8 Sep. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/587,018, entitled PERSONALIZED PLAN DEVELOPMENT BASED ON OUTCOME IDENTIFICATION, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 29 Sep. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/587,127, entitled PERSONALIZED PLAN DEVELOPMENT BASED ON OUTCOME IDENTIFICATION, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 30 Sep. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/590,027, entitled PERSONALIZED PLAN DEVELOPMENT BASED ON ONE OR MORE REPORTED ASPECTS' ASSOCIATION WITH ONE OR MORE SOURCE USERS, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 29 Oct. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/590,039, entitled PERSONALIZED PLAN DEVELOPMENT BASED ON ONE OR MORE REPORTED ASPECTS' ASSOCIATION WITH ONE OR MORE SOURCE USERS, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 30 Oct. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/590,600, entitled PERSONALIZED PLAN DEVELOPMENT BASED ON IDENTIFICATION OF ONE OR MORE RELEVANT REPORTED ASPECTS, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 10 Nov. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/590,841, entitled PERSONALIZED PLAN DEVELOPMENT BASED ON IDENTIFICATION OF ONE OR MORE RELEVANT REPORTED ASPECTS, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 12 Nov. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/592,075, entitled DEVELOPMENT OF PERSONALIZED PLANS BASED ON ACQUISITION OF RELEVANT REPORTED ASPECTS, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 17 Nov. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/592,161, entitled DEVELOPMENT OF PERSONALIZED PLANS BASED ON ACQUISITION OF RELEVANT REPORTED ASPECTS, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 18 Nov. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/592,544, entitled IDENTIFICATION AND PROVISION OF REPORTED ASPECTS THAT ARE RELEVANT WITH RESPECT TO ACHIEVEMENT OF TARGET OUTCOMES, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 24 Nov. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/592,548, entitled IDENTIFICATION AND PROVISION OF REPORTED ASPECTS THAT ARE RELEVANT WITH RESPECT TO ACHIEVEMENT OF TARGET OUTCOMES, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 25 Nov. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/592,944, entitled TEMPLATE DEVELOPMENT BASED ON SENSOR ORIGINATED REPORTED ASPECTS, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 3 Dec. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/592,946, entitled TEMPLATE DEVELOPMENT BASED ON SENSOR ORIGINATED REPORTED ASPECTS, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 4 Dec. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/653,117, entitled SOURCE USER BASED PROVISION OF ONE OR MORE TEMPLATES, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 7 Dec. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/653,180, entitled SOURCE USER BASED PROVISION OF ONE OR MORE TEMPLATES, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 8 Dec. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/653,387, entitled TARGET OUTCOME BASED PROVISION OF ONE OR MORE TEMPLATES, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 10 Dec. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/653,386, entitled TARGET OUTCOME BASED PROVISION OF ONE OR MORE TEMPLATES, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 11 Dec. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/653,972, entitled DETECTING DEVIATION FROM COMPLIANT EXECUTION OF A TEMPLATE, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 17 Dec. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/655,075, entitled DETECTING DEVIATION FROM COMPLIANT EXECU- TION OF A TEMPLATE, naming Shawn P. Firminger; Jason Garms; Roderick A. Hyde; Edward K. Y. Jung; Chris D. Karkanias; Eric C. Leuthardt; Royce A. Levien; Richard T. Lord; Robert W. Lord; Mark A. Malamud; John D. Rinaldo, Jr.; Clarence T. Tegreene; Kristin M. Tolle; Lowell L. Wood, Jr. as inventors, filed 21 Dec. 2009, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

SUMMARY

A computationally implemented method includes, but is not limited to determining whether a plurality of end users deviated from compliantly executing a template designed to facilitate the plurality of end users in achieving one or more target outcomes when one or more emulatable aspects included in the template are emulated by the plurality of end users, the one or more emulatable aspects being based on one or more relevant reported aspects of one or more source users that were deemed to have been relevant to achieving the one or more target outcomes; and modifying the template based, at least in part, on determining that the plurality of end users deviated from compliantly executing the template. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

A computationally implemented system includes, but is not limited to: means for determining whether a plurality of end users deviated from compliantly executing a template designed to facilitate the plurality of end users in achieving one or more target outcomes when one or more emulatable aspects included in the template are emulated by the plurality of end users, the one or more emulatable aspects being based on one or more relevant reported aspects of one or more source users that were deemed to have been relevant to achieving the one or more target outcomes; and means for modifying the template based, at least in part, on determining that the plurality of end users deviated from compliantly executing the template. In addition to the foregoing, other system aspects are described in the claims, drawings, and text forming a part of the present disclosure.

A computationally implemented system includes, but is not limited to: circuitry for determining whether a plurality of end users deviated from compliantly executing a template designed to facilitate the plurality of end users in achieving one or more target outcomes when one or more emulatable aspects included in the template are emulated by the plurality of end users, the one or more emulatable aspects being based on one or more relevant reported aspects of one or more source users that were deemed to have been relevant to achieving the one or more target outcomes; and circuitry for modifying the template based, at least in part, on determining that the plurality of end users deviated from compliantly executing the template. In addition to the foregoing, other system aspects are described in the claims, drawings, and text forming a part of the present disclosure.

A computer program product including a signal-bearing medium bearing one or more instructions for determining whether a plurality of end users deviated from compliantly executing a template designed to facilitate the plurality of end users in achieving one or more target outcomes when one or more emulatable aspects included in the template are emulated by the plurality of end users, the one or more emulatable aspects being based on one or more relevant reported aspects of one or more source users that were deemed to have been relevant to achieving the one or more target outcomes; and one or more instructions for modifying the template based, at least in part, on determining that the plurality of end users deviated from compliantly executing the template. In addition to the foregoing, other computer program product aspects are described in the claims, drawings, and text forming a part of the present disclosure.

A method for modifying a template based, at least in part, on determining whether a plurality of end users deviated from compliantly executing the template, the method includes determining whether a plurality of end users deviated from compliantly executing a template designed to facilitate the plurality of end users in achieving one or more target outcomes when one or more emulatable aspects included in the template are emulated by the plurality of end users, the one or more emulatable aspects being based on one or more relevant reported aspects of one or more source users that were deemed to have been relevant to achieving the one or more target outcomes; and modifying, using a processor, the template based, at least in part, on determining that the plurality of end users deviated from compliantly executing the template.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 2*b* shows another perspective of the Template Modifying Module 104 of the Computing Device 10 of FIG. 1*b*.

DETAILED DESCRIPTION

Figure 1A:
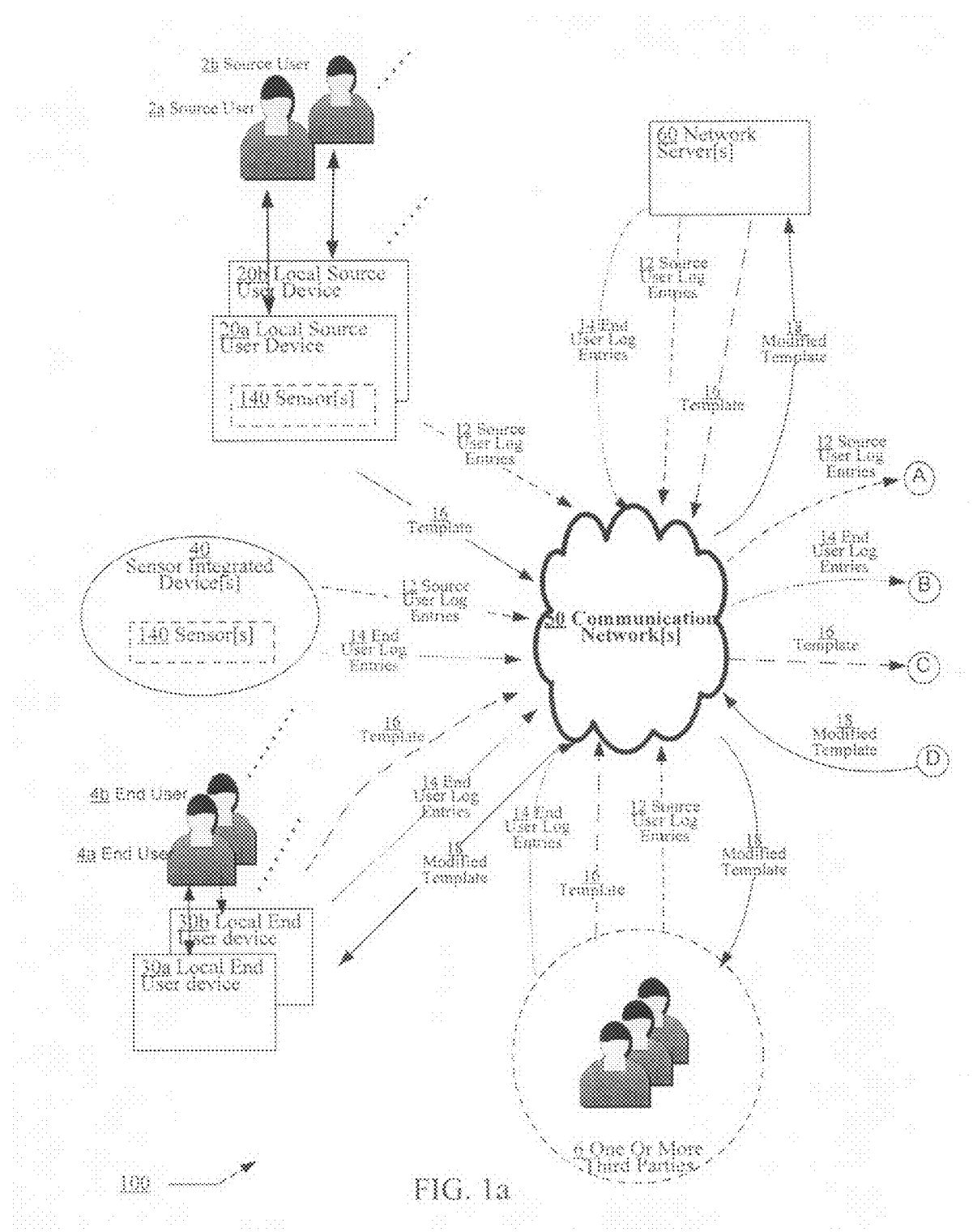
FIGS. 1*a* and 1*b* show a high-level block diagram of a Computing Device 10 operating in a network environment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

A recent trend that has enjoyed explosive popularity in the computing/communication field is to electronically record one's daily activities, behaviors, thoughts, beliefs, traits, physical or mental states, physical characteristics, and other aspects of the person's everyday life onto an open journal. One place where such open journals are maintained is at social networking sites commonly known as "blogs" where one or more users may report or post every aspect of their daily lives. In brief, an "aspect," as will be referred to herein, may be in reference to any act, behavior, characteristic, user state or status, belief, external events, and so forth, that may be associated with a user (e.g., a person including, for example, a network user such as a blogger or a social networking user). The process of reporting or posting blog entries is commonly referred to as "blogging." A newer type of blogging that has become very popular in recent times is microblogging, otherwise known as "twittering" or "tweeting." In microblogging, each of the microblogs that are posted are typically relatively short posts or entries, usually not more than 140 characters long.

Other types of social networking sites may also allow users to maintain open journals and to allow users to easily update their personal information in real time. Such updates are typically made via, for example, social networking status reports otherwise known simply as "status reports." These social networking sites allow a user to report or post for others to view the latest status or other aspects related to the user.

Another recent tread in social networking is to employ one or more sensors to detect and report on a wide variety of user aspects (i.e., aspects of a user). Examples of sensors that may be used for such purposes vary widely, ranging from well-known devices that can detect and report on various physiological parameters such as heart rate or blood pressure, to sensors that can detect certain user behaviors or activities such as toilet usage. Examples of sensors that may be employed in order to monitor or detect user activities include, for example, accelerometers, pedometers, global positioning systems or GPSs, and so forth. Such devices are already, in fact, being integrated into mobile computing/communication devices such as cellular telephones and smart phones, and even into functional devices such as automobiles, exercise machines, household appliances, and so forth.

Other types of sensors are also being integrated into mobile computing/communication devices such as those that monitor environmental conditions. Examples of such sensors include, for example, those that can measure atmospheric conditions such as air quality levels. In some cases, sensors may be integrated into functional devices such as automobiles, exercise machines, household appliances, and so forth in order to detect and monitor their usage. There are also sensors that are currently available that can even monitor bathroom or toilet usage. All the above described sensors may be configured to provide their collected data through log entries such as entries made through social networking channels (e.g., microblogs, blogs, social networking internet sites, and so forth).

Although a wealth of personal information provided through log entries (e.g., microblogs, status reports, and so forth) are now available through such social networking internet sites (or simply "social networking sites"), it is only recently has there been any effort to exploit such potentially useful data. As blogs, microblogs, and various social networking sites become increasingly popular, personal data collected through such means may be spread across multiple network locations.

One possible way to exploit such personal data is to use such data to develop templates for achieving a variety of target outcomes (e.g., goals) based on the personal data. In brief, a template may be a plan, a program, or a schedule that is designed to facilitate one or more end users to achieve one or more target outcomes when one or more "emulatable aspects" that may be included with the template are emulated. In other words, to use personal data of those (e.g., source users) who have already achieved desirable goals (e.g., target outcomes) to develop templates for others (e.g., end users) to emulate in order to facilitate the others in achieving those goals.

Each of the one or more emulatable aspects that may be included in a template may be based on and correspond to one or more reported aspects of one or more source users that may have been reported through, for example, social networking channels (e.g., microblogs, social networking sites, and so forth). An "aspect," in brief may be any behavior, act, mental state, physical state, and so forth that may be associated with a source user. A "reported aspect" is any aspect associated with a source user that may have been reported via, for example, one or more social networking channels or by other means.

There are at least two types of templates that could be developed from personal data obtained through, for example, social networking channels. One type of templates are generic templates that may not be designed for use by any particular end user or a particular group of end users but instead may be designed to be used by any random user in order to achieve one or more target outcomes. The second type of templates, which may be referred to as personalized templates or personalized plans, include those templates that have been personalized for use by a particular end user or users (e.g., a modified version of a generic template that has been modified in order to accommodate the end user's limitations and/or preferences). For purposes of this description, references to a "template" in the following will be in reference to either the first or the second type of templates.

In any event, once a template for achieving one or more target outcomes has been developed, the developed template, which could be a generic template or a personalized template, may be provided to one or more end users. An end user may then compliantly execute (i.e., properly execute) the provided template by fully or partially emulating all or some of the one or more emulatable aspects that may be included in the template in order to achieve the one or more target outcomes. Of course, if an end user is unable to compliantly emulate the template, than the one or more target outcomes associated with the template may or may not be realized. In many cases, however, it may still be possible to achieve the target outcomes associated with templates even if end users do not compliantly execute the templates.

What constitutes compliant execution of a template will depend on a number of factors including, for example, the type of template being emulated and the number and type of emulatable aspects that may be included in the template. For example, in some cases, the compliant execution of a template may require full and complete emulation of each of the one or more emulatable aspects that may be included in the template (e.g., if the template requires 45 minutes of running every other day for two months, than to compliantly emulate the template an end user must execute 45 minutes of running every other day for two months).

In other cases, however, the compliant execution of a template may merely require that each of the one or more emulatable aspects that may be included in the template be at least substantially emulated or at least only partially emulated (e.g., in the same example above, a compliant execution of the template may be achieved if, for example, on some occasions the end user runs 30 minutes rather than 45 minutes). In still other cases, the compliant execution of a template may only require that a substantial portion of a plurality of emulatable aspects that may be included in the template be fully or substantially emulated (e.g., in the above example, a compliant execution of the template may be achieved even if one or more two days of running are not emulated by the end user).

For purposes of this description, and unless indicated otherwise, the phrase "compliant execution of a template" may be in reference to a complete or substantially complete emulation of each of the one or more emulatable aspects that may be included the template. Further, in some cases, the "compliant execution of a template" may be in reference to a plurality of emulatable aspects that may be included in the template to be completely or substantially completely emulated in the order (e.g., sequential order) that is specified by the template.

In some cases, it may be possible to achieve one or more target outcomes of a template without strictly or compliantly executing the template. That is, upon end users executing a particular template, some end users may deviate from complete and total emulation of each of the one or more emulatable aspects that may be included in the particular template while still achieving the target outcomes.

In various embodiments, methods, systems, circuitry, and computer program products are provided that are designed to modify a template based on feedback provided by end users. More particularly, the methods, systems, circuitry, and computer program products may be designed to, among other things, modify a template based, at least in part, on determining that a plurality of end users deviated from compliantly executing the template. In some embodiments, the determining of the deviation may involve, for example, at least acquiring and processing log entry data (e.g., as acquired through blogs, microblogs, social networking interne sites, and so forth) associated with those end users who have deviated from the compliant execution of the template while still achieving the one or more target outcomes associated with the template. In some embodiments, the modification of the template may be based, at least, on the processing of the log entry data.

As previously described a "template" may be any type of plan, program, or schedule that is designed to facilitate achievement of one or more target outcomes when one or more emulatable aspects included in the template are emulated. Of course, and as briefly described above, in some cases, it may also be possible to achieve one or more target outcomes of a template without fully emulating all of the one or more emulatable aspects that may be included in the template or even failing to emulate a portion of a plurality of emulatable aspects that may be included in the template. As also indicated earlier, the one or more emulatable aspects that may be included in a template may be based on and correspond to one or more reported aspects of one or more source users, who may or may not be the source for the one or more reported aspects. That is, a reported aspect may be reported by any one of a number of different sources including, for example, by the source user (e.g., a microblogger or a social networking user) who is the basis for the reported aspect, by a sensor, or by a third party (e.g., such as another source user). Similarly, reported aspects of an end user, such as reported aspects of the end user while the end user is executing a template, may also be provided by a number of different sources. Such reported aspects of the end user may be used, in some cases, as end user feedback in order to modify or further develop a template.

As described, a template may comprise of one or more emulatable aspects that may be based on reported aspects of, for example, a particular source user. Note that the word "emulatable" as will be repeatedly used herein has no relevant meaning other than to be used in the following description to merely distinguish those aspects (emulatable aspects) that are indicated in a template from other types of aspects (e.g., reported aspects of source users or end users). In accordance with various embodiments, a template may be developed for achieving almost any type of desired outcome (e.g., target outcome) so long as the appropriate data, such as log entry data of source users who have achieved the desired outcome, are available. Examples of the types of templates that could be developed based on log entry data include, for example, those that are designed to facilitate achievement of medical or health related outcomes, those that are designed to facilitate achievement of athletic or gaming outcomes, those that designed to facilitate achievement of particular user states such as mental or social states, those that are designed to facilitate achievement of intellectual or academic outcomes, and so forth.

In some cases, a template may merely indicate or be a collection of one or more emulatable aspects that end users may emulate in order to achieve one or more target outcomes. In other cases, however, a template may indicate a plurality of emulatable aspects as well as define their relationships (e.g., temporal or specific time relationship) with respect to each other. Such a template will be very similar to a schedule or program that indicates when each of the emulatable aspects included in the template should be emulated by end users with respect to the other emulatable aspects included in the template. For example, if a template is designed to facilitate end users to shed a certain amount of body weight, it may include a schedule of when and what activities (e.g., go jogging for 30 minutes on day 1, go swimming for 40 minutes on day 2, and so forth) end users may need to execute in order to achieve the weight loss. Similarly, if the template is designed to, for example, facilitate end users to achieve a high score for the scholastic aptitude test (SAT), the template may be a schedule of when and what activities (e.g., read a particular book on day 1, work on math problems from a particular math book on day 2, and so forth) end users may need to execute in order to achieve the high test score for the SAT.

In some instances a template may include one or more emulatable intermediate outcomes that are related to the one or more target outcomes associated with the template. For example, in the above weight loss example, the template may indicate the amount of weight loss end users should have achieved (e.g., in order to achieve the target outcome) after emulating, for example, one week, two weeks, or a month of emulatable aspects indicated by the template.

In still other cases, a template may merely be a collection of emulatable aspects that does not define the relationships between the emulatable aspects. For example, a template designed to facilitate an end user to achieve relaxed state of mind may indicate two unlinked emulatable aspects, "get 8 hours of sleep each night," and "avoid caffeine beverages." Such a template would not necessarily have any indication of relationship between the two emulatable aspects indicated by the template. It should be noted here that an emulatable aspect that may be included into a template may not only be an act or a behavior, but may be a physiological characteristic, a mental state, or any other aspect that may be emulated. For example, a template that is designed to facilitate reducing backaches may include as one of its aspects, a requirement to keep blood pressure below a certain level, which is a physiological state. An emulatable aspect may even be an external event, such as environmental conditions, that an end user may have some control over.

In some embodiments, a template may include or be linked to other information other than emulatable aspects. For example, in some instances, a template may include or be associated with a particular source user and/or with a particular target outcome. Other information may also be included with or be associated with a template as will be further described herein.

In order to facilitate understanding of the various concepts to be described herein, an introduction to the meaning of certain words and phrases to be used in the following discussion will now be provided. In brief, and as will be further described herein, an "aspect" may be any occurrence of any behavior, act, belief, characteristic, state, external event, or any other facet associated with a source user or a group of source users. A "source user" may be any person, such as a microblogger or a social networking user, who may be the basis for one or more reported aspects. Note that a source user may not necessarily have to be the source for the one or more reported aspects that are related to the source user since reported aspects that are associated with a particular source user may be provided by other source users or by sensors.

A "reported aspect" may be any aspect associated with or related to a source user or an end user that has been reported by, for example, the source user, the end user, by one or more sensors, or one or more third parties (e.g., other source users or end users). In some instances, such a reported aspect may be reported in the form of a log entry such as a microblog entry, a status report, or a journal entry.

A "target outcome" may be any type of desirable goal or result that may be sought by, for example, end users. Examples of target outcomes include, for example, health-related outcomes such as weight loss or improved cardiovascular conditioning, athletic outcomes such as developing a particular athletic skill including being able to pitch a curve ball or achieving a particular golf handicap, physiological outcomes such as reduced blood pressure or blood glucose levels, social outcomes such as obtaining membership into an elite social club or attaining a particular social status, mental state outcomes such as achieving certain level of calmness or happiness, interpersonal or relational outcomes such as having lots of friends or developing skill to make friends, employment outcomes such as being promoted or developing certain work skills, academic or intellectual outcomes, and so forth.

An "end user" may be any person, for example, who executes a template in order to achieve one or more target outcomes. As briefly described above, a "source user" may be any person who may be the basis for one or more reported aspects. Note that although in most cases, a source user will be an actual (real) person who may be the basis for one or more reported aspects, in other cases, however, a source user may be a fictional person such as a composite of multiple "actual" source users. For example, reported aspects indicating actual aspects of a plurality of actual source users may be compiled and processed (e.g., normalized or averaged out) in order to create a fictional source user.

Figure 1B:
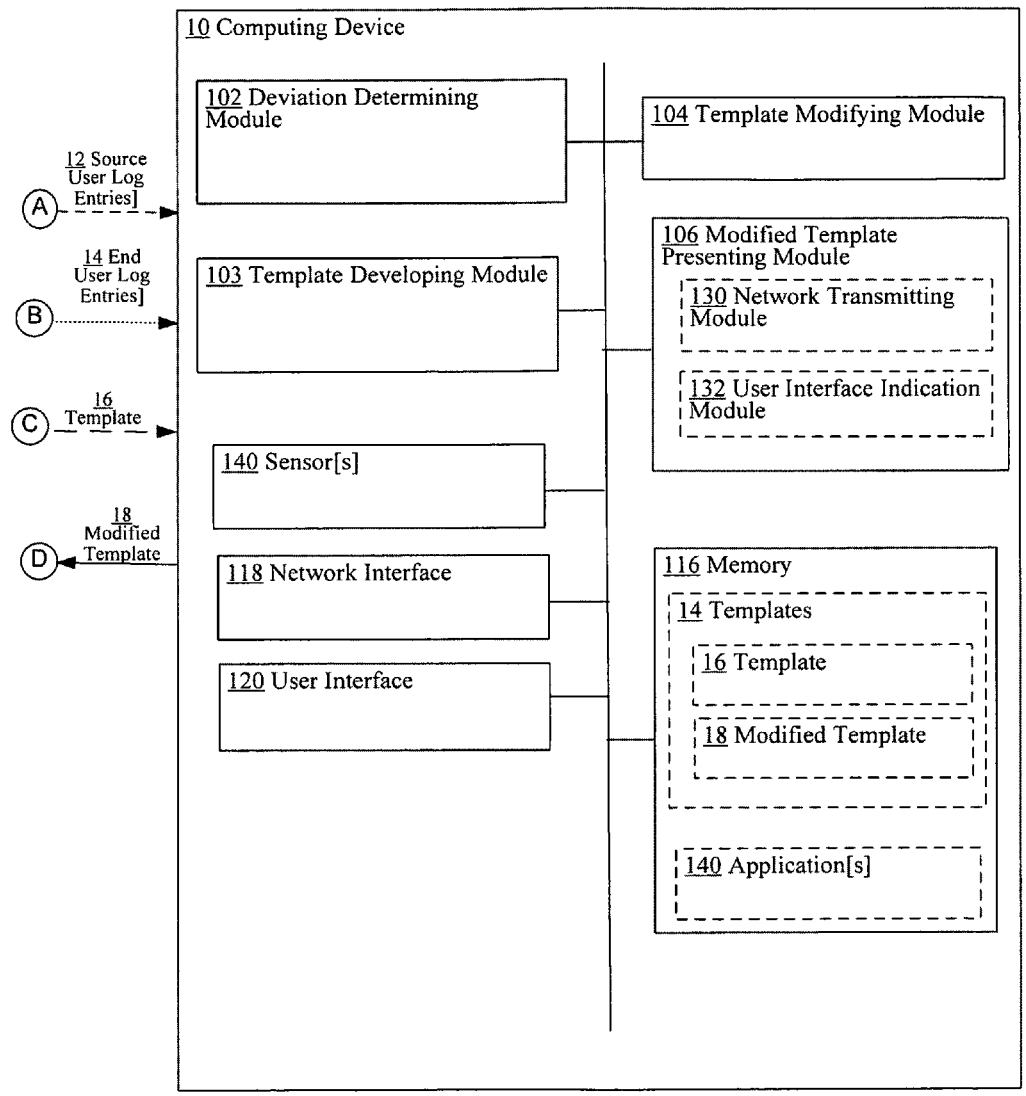

Turning now to FIGS. 1a, and 1b illustrating an example environment in which the methods, systems, circuitry, and computer program products in accordance with various embodiments may be implemented by a computing device 10. In particular, the methods, systems, circuitry, and computer program products may be implemented at any network device including at a peer-to-peer network component device. In some embodiments, the computing device 10 may be a server such as one of the one or more network servers 60 illustrated in FIG. 1a. Alternatively, the computing device 10 may be a source user device such as one of the local source user devices 20* illustrated in FIG. 1a. In still other embodiments, the computing device 10 may be an end user device such as one of the local end user device 30* illustrated in FIG. 1a. Note that in the following, "*" represents a wildcard. Thus, references in the following description to, for example, "a source user 2*" may be in reference to a source user 2a, a source user 2b, and so forth, or a combination thereof.

Note further that for ease of understanding and explanation, the computing device 10 of the exemplary environment 100 of FIGS. 1a and 1b in the following discussion will be generally described operating as a server (e.g., server embodiment) rather than as an end user device or as a source user device. Further, although the following discussion related to the exemplary environment 100 of FIGS. 1a and 1b assumes that the computing device 10 is a server, the following discussion will, for the most part, be applicable even if the computing device 10 were operating as an end user device (e.g., local end user device 30*) or as a source user device (e.g., local source user device 20*) with certain obvious exceptions (e.g., if the computing device 10 is an end user device or a source user device rather than a server, the computing device 10 may communicate with an end user 4* or a source user 2* directly through a user interface 120 rather than indirectly through one or more communication networks 50 as may be the case when the computing device 10 is a server). In some embodiments, the computing device 10 may operate via a web 1.0 or web 2.0 construct.

Referring back to FIGS. 1a and 1b, and as previously indicated, the computing device 10 may be a network device such as a server (e.g., a network server 60) that is designed to communicate with other network devices. For example, the computing device 10 may communicate with one or more source users 2*(e.g., source user 2a, source user 2b, and so forth) through one or more local source user devices 20*(e.g., local source user device 20a, local source user device 20b, and so forth), with a plurality of end users 4*(e.g., end user 4a, end user 4b, and so forth) through a plurality of local end user devices 30*(e.g., local end user device 30a, local end user device 30b, and so forth), with one or more sensor integrated devices 40 (e.g., a transportation vehicle such as a car, an exercise machine, or any other type of functional device that may have an integrated sensor designed to sense, for example, usage), with one or more network servers 60, and/or with one or more third parties 6 (e.g., one or more content providers, one or more network service providers, and/or one or more other end users 4) via one or more communication networks 50. In some implementations, the one or more communication networks 50 may include one or more wireless networks and/or one or more wired networks including, for example, at least one of a local area network (LAN), a wireless local area network (WLAN), personal area network (PAN), Worldwide Interoperability for Microwave Access (WiMAX), public switched telephone network (PTSN), general packet radio service (GPRS), cellular networks, and/or other types of wireless and/or wired networks.

In some implementations, the computing device 10 may be designed to develop at least one template 16 that is designed to facilitate achievement of one or more target outcomes when one or more emulatable aspects included in the template 16 are emulated. The development of the template 16 may be based on one or more source user log entries 12 that may indicate one or more reported aspects associated with one or more source users 2* and that may be received from a variety of sources including for example, one or more network servers 60, one or more local source user devices 20*, one or more sensor integrated devices 40, and/or one or more third parties 6. In some cases, such source user log entries 12 may be in the form of, for example, social networking entries such as blog entries (e.g., microblog entries), status reports, and so forth. After receiving the one or more source user log entries 12 indicating the one or more reported aspects associated with the one or more source user 2*, the template 16 may be developed by at least identifying from the one or more reported aspects one or more relevant reported aspects that are deemed to be relevant to achieving the one or more target outcomes. Once the relevant reported aspects have been identified, the template 16 may be developed (e.g., created) by at least including into the template 16 one or more emulatable aspects that correspond to the one or more relevant reported aspects. In some cases, the development of the template 16 may further include defining in the template 16 the relationships (e.g., temporal or specific time relationships) between a plurality of emulatable aspects that may be included in the template 16.

After developing the template 16, the template 16 may be provided to at least one end user 4, to one or more network servers 60, to one or more third parties 6, or to one or more source users 2* via one or more communication networks 50. In embodiments in which the computing device 10 is a local client device such as local end user device 30* or a local source user device 20*, the template 16 may be presented via a user interface 120.

In alternative implementations, however, the template 16 may not be developed at the computing device 10, but instead, may be provided to the computing device 10 from a remote network site (e.g., a local source user device 20*, a network server 60, a local end user device 30*, and so forth) through, for example, one or more communication networks 50.

In various implementations, after developing or being provided with a template 16, the computing device 10 may be designed to monitor the progress of, for example, a plurality of end users 4*in compliantly executing the template 16 in order to achieve the one or more target outcomes associated with the template 16. In particular, such monitoring may be performed in order to determine any deviation by the end users 4* from a compliant execution of the template 16.

In order to monitor the progress of the end users 4* in compliantly executing the template 16, the computing device 10 may be designed to receive one or more end user log entries 14 (e.g., in the form of, for example, microblogs, status reports, journal entries, sensor entries, and so forth) associated with the end users 4* from one or more sources (e.g., local end user devices 30*, one or more sensor integrated devices 40, one or more third parties 6 such as other end users 4* and/or one or more network servers 60). The end user log entries 14 to be received may indicate a plurality of reported aspects of a plurality of end users 4* when the end users 4* are, for example, executing the template 16. Note that in embodiments in which the computing device 10 is an end user device (e.g., local end user device 30), one or more of the end user log entries 14 may be received directly from an end user 4* via the user interface 120.

In order to determine deviation from the compliant execution of the template 16 by the plurality of end users 4*, the reported aspects indicated by the received end user log entries 14 may be compared to the one or more emulatable aspects of the template 16. By making the comparison, a determination may be made as to whether one or more deviations from the one or more emulatable aspects included in the template 16 may have occurred. By at least determining that one or more deviations from the one or more emulatable aspects of the template 16 have occurred, a determination may be made that one or more deviations from the compliant emulation of the template 16 may have also occurred.

In any event, after determining or detecting deviation from the compliant execution of the template 16 by a plurality of end users 4*, the computing device 10 may be designed to modify the template 16 resulting in a modified template 18. The template 16 may be modified in a number of different ways in various alternative implementations. For example, in some implementations, the template 16 may be modified by modifying at least one of one or more emulatable aspects included in the template 16. In some instances, the modification of at least one of the one or more emulatable aspects may involve revising at least one of the one or more emulatable aspects, replacing at least one of the one or more emulatable aspects with one or more replacement or substitute emulatable aspects, or deleting at least one of the one or more emulatable aspects. In some implementations, a template 16 may be modified by adding one or more additional emulatable aspects. In implementations where a template 16 includes multiple emulatable aspects, the template 16 may be modified by modifying the one or more relationships (e.g., temporal or specific time relationships) between the plurality of emulatable aspects included in the template 16. Other ways of modifying a template 16 may also be employed in various alternative implementations.

In some implementations, the template 16 may be modified (e.g., by substituting or modifying existing emulatable aspects, or by adding additional emulatable aspects) in order to include at least one plausible emulatable aspect that was successfully emulated by at least a portion of a plurality of end users 4* who were determined to have deviated from the compliant execution of the template 16. In the same or different implementations, the template 16 may be modified in order to include at least one emulatable aspect that was developed by processing reports aspects (e.g., as indicated by end user log entries 14) of end users 4* who were determined to have deviated from the compliant execution of the template 16. These various approaches for modifying a template 16 as well as other approaches for modifying the template 16 will be discussed in greater detail herein. In some implementations, the template 16 may be modified to include one or more emulatable aspects belonging to a wide variety of emulatable aspect types (e.g., emulatable behaviors such as emulatable user activities, user attitudes, and user conduct, emulatable user beliefs, emulatable user states, and so forth).

As a result of modifying the template 16, a modified template 18 may be generated by the computing device 10. In some cases, the modified template 18 may be presented to, for example, at least one of the end users 4*, one or more network servers 60, and/or one or more third parties 6 via the one or more communication networks 50 and/or via the user interface 120.

In various embodiments, the computing device 10, as previously indicated, may be a server (e.g., one of the one or more network servers 60) that may be located at a single network site, located across multiple network sites, or may be a conglomeration of servers located at multiple network sites. In embodiments in which the computing device 10 is a source user device (e.g., local source user device 20*) or an end user device (e.g., local end user device 30*) rather than a network server 60, the computing device 10 may be any one of a wide range of mobile or stationary computing/communication devices including, for example, a laptop, a desktop, a workstation, a cellular telephone, a personal digital assistant (PDA), a Smartphone, a web tablet such as a Netbook, and so forth.

Referring back to the exemplary environment 100 of FIGS. 1a and 1b, the one or more sensor integrated devices 40 of the exemplary environment 100 of FIGS. 1a and 1b may directly communicate with the one or more communication networks 50 in various embodiments. Alternatively, the one or more sensor integrated devices 40 may indirectly communicate with the one or more communication networks 50 via the one or more local source user devices 20* or via the one or more local end user devices 30*(e.g., via, for example, personal area network or PAN). In various embodiments, a sensor integrated device 40 may be a variety of functional devices that may comprise of one or more sensors 140 and that may be operated or used by a source user 2* or by an end user 4*. Examples of such devices include, for example, a transportation vehicle (e.g., automobile, a motorcycle, a boat, a plane, and so forth), an exercise machine (e.g., a treadmill), a household appliance (e.g., television set), and so forth.

As will be further described herein, the one or more sensors 140, which may also be included in the one or more local source user devices 20*, the local end user devices 30*, and/or the computing device 10, may include any type of sensors 140 that can sense one or more aspects of a source user 2* or an end user 4*. Examples of such sensors 140 include, for example, sensors 140 that can sense various physical characteristics of a source user 2* or an end user 4*(e.g., heart rate sensor or blood pressure sensor), sensors 140 that can sense activities of a source user 2* or an end user 4*(e.g., a pedometer, an accelerometer, and so forth), sensors 140 that can sense environment conditions (e.g., air quality sensors), sensors 140 that can sense the location of a source user 2* or an end user 4*(e.g., global positioning system or GPS), sensors 140 that can provide physiological data that may be processed in order to determine inferred mental states of source or end users 2* or 4*, and so forth.

Each of the one or more local source user devices 20* and the local end user devices 30*(as well as the computing device 10 in embodiments in which the computing device 10 is an end user device or a source user device) may be any one of a variety of computing/communication devices including, for example, a cellular phone, a personal digital assistant (PDA), a laptop, a desktop, or other types of computing/communication devices. In some embodiments, the one or more local source user devices 20* and/or the local end user devices 30*(as well as the computing device 10 in some embodiments) may be a handheld device such as a cellular telephone, a Smartphone, a Mobile Internet Device (MID), an Ultra Mobile Personal Computer (UMPC), a convergent device such as a personal digital assistant (PDA), and so forth. Alternatively, such local client devices (e.g., local source user device 20* and/or local end user devices 30*) may be a laptop, a desktop, a workstation, a web tablet such as a Netbook, or other types of devices that may not be a handheld device in various alternative implementations.

Figure 2A:
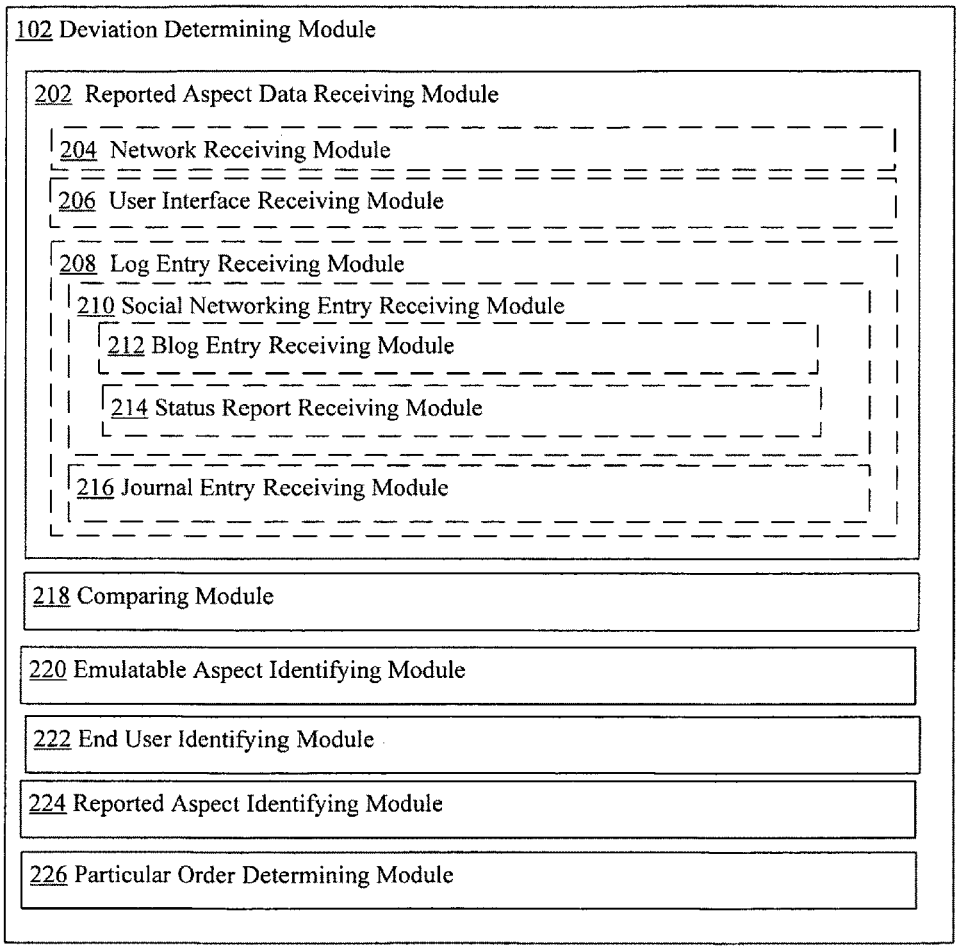
FIG. 2*a* shows another perspective of the Deviation Determining Module 102 of the Computing Device 10 of FIG. 1*b*.

The computing device 10 as illustrated in FIG. 1b may include one or more modules, sub-modules, and various other components. As shown, the computing device 10 may include at least a deviation determining module 102 (which may further include one or more sub-modules as illustrated in FIG. 2a) and a template modifying module 104 (which may also include one or more sub-modules as illustrated in FIG. 2b). The deviation determining module 102 may be particular configured to, among other things, determine whether a plurality of end users 4* deviated from compliantly executing a template 16 designed to facilitate the plurality of end users 4* in achieving one or more target outcomes when one or more emulatable aspects included in the template 16 are emulated by the plurality of end users 4*, the one or more emulatable aspects being based on one or more relevant reported aspects of one or more source users 2* that were deemed to have been relevant to achieving the one or more target outcomes. In contrast, the template modifying module 104 may be particularly configured to, among other things, modify the template 16 based, at least in part, on determining that the plurality of end users 4* deviated from compliantly executing the template 16.

In various implementations, the computing device 10 may further include a template developing module 103 and a memory 116. The template developing module 103 may be particularly configured to develop one or more templates 16 by at least initially identifying or determining one or more relevant reported aspects of one or more source user 2* that have been determined to be relevant for achieving one or more target outcomes. After identifying one or more relevant reported aspects, the template developing module 103 may be particularly configured to develop (e.g., create) a template 16 by at least including into the template 16 one or more emulatable aspects that correspond to the one or more identified relevant reported aspects. The determination of relevancy of a reported aspect associated with one of the source users 2* may be based on a number of factors including, for example, whether it is a type of reported aspect that is of interest to end users 4* or source users 2* and whether the reported aspect occurred proximate to the occurrence of the one or more target outcomes as achieved by the source user 2*.

The memory 116, in various implementations, may store a plurality of templates 14 including a template 16 and/or a modified template 18 that is a modified version of template 16. In some implementations, the memory 116 may store one or more applications 140 (e.g., a text messaging application, an instant messaging application, an email application, a social networking application, a voice recognition system, a Web 1.0 application, and/or Web 2.0 application to facilitate in communicating via, for example, the World Wide Web). The memory 116 may comprise of one or more of a mass storage device, a read-only memory (ROM), a programmable read-only memory (PROM), an erasable programmable read-only memory (EPROM), a cache memory such as random access memory (RAM), a flash memory, a synchronous random access memory (SRAM), a dynamic random access memory (DRAM), and/or other types of memory devices.

The computing device 10 may also include, in various implementations, a network interface 118 (e.g., a network interface card or NIC), a user interface 120 (e.g., a display monitor, a touchscreen, a microphone, a speaker, a mouse, and so forth), and/or one or more sensors 140 that are designed to measure or sense one or more user aspects. Examples of sensors 140 include, for example, devices that are designed to sense user activities such as pedometers and accelerometers, devices that are designed to sense physiological characteristics such as heart rate monitors or blood glucose monitors, devices that are designed to sense environmental conditions such as sensors 140 for measuring air quality, devices that are designed to detect user location such as GPS, and so forth. In some cases, the presence or absence of some of these modules and components of computing device 10 may depend on, for example, whether the computing device 10 is a server, an end user device, or a source user device. For example, if the computing device 10 is a server, then the computing device 10 may not include a user interface 120.

FIG. 2a illustrates particular implementations of the deviation determining module 102 of FIG. 1b. The deviation determining module 102 in various implementations may include, among other things, a reported aspect data receiving module 202 particularly configured for, among other things, receiving data indicating reported aspects of end users 4*, a comparing module 218 particularly configured to compare reported aspects of end users 4* with one or more emulatable aspects included in a template 16, and/or an emulatable aspect identifying module 220 particularly configured to, among other things, identify which of the one or more emulatable aspects included in template 16 were not emulated at all or only partially emulated by one or more of the end users 4* based on the comparison of the reported aspects with the one or more emulatable aspects included in the template 16.

The deviation determining module 102 may also include, in various implementations, an end user identifying module 222 particularly configured to, among other things, identify which of the plurality of end users 4* did not emulate at all or only partially emulated the one or more emulatable aspects included in the template 16 that were identified by the emulatable aspect identifying module 220 as being not emulated at all or were only partially emulated by one or more of the end users 4*, a reported aspect identifying module 224 particularly configured to, among other things, identify which of the reported aspects of the plurality of end users 4* represent one or more replacement aspects for one or more emulatable aspects included in the template 16, and/or a particular order determining module 226 that is specifically designed to, among other things, determine whether the plurality of end users 4* did not emulate a plurality of emulatable aspects included in the template 16 in a particular order as defined by the template 16.

In various implementations, the reported aspect data receiving module 202 may further include one or more sub-modules including for example, a network receiving module 204 (designed to, among other things, receive data indicating at least one reported aspect associated with at least one end user 4* from one or more communication networks 50), a user interface receiving module 206 (designed to, among other things, receive at least one reported aspect associated with at least one end user 4* via a user interface 120), and/or a log entry receiving module 208 (designed to, among other things, receive data indicating at least one reported aspect associated with at least one end user 4* via one or more end user log entries 14).

The log entry receiving module 208, in various implementations, may further include a social networking entry receiving module 210 (which may further include a blog entry receiving module 212 and/or a status report receiving module 214) and/or a journal entry receiving module 216. The social networking entry receiving module 210 may be configured to receive the data indicating the at least one reported aspect associated with the at least one end user 4* via one or more social networking entries. The blog entry receiving module 212 may be configured to receive the data indicating the at least one reported aspect associated with the at least one end user 4* via one or more blog entries. The status report receiving module 214 may be configured to receive the data indicating the at least one reported aspect associated with the at least one end user 4* via one or more social networking status reports. The journal entry receiving module 216, in contrast, may be configured to receive the data indicating the at least one reported aspect associated with the at least one end user 4* via one or more journal entries.

FIG. 2b illustrates particular implementations of the template modifying module 104 of the computing device 10 of FIG. 1b. As illustrated, the template modifying module 104 may include, in various implementations, an emulatable aspect modifying module 230 (which may further include an emulatable aspect revising module 232, an emulatable aspect replacing module 234, and/or an emulatable aspect deleting module 236). As further illustrated, in some implementations the template modifying module 104 may also include an emulatable aspect adding module 238 (which may further include a relationship defining module 240), a relationship modifying module 242, and/or a reported aspect analyzing module 243. In some implementations the reported aspect analyzing module 243 may further include a mean value emulatable aspect developing module 246 and/or an average value emulatable aspect developing module 248. These modules and sub-module of the template modifying module 104, as well as the modules and sub-modules of the deviation determining module 102 of FIG. 2a, will be discussed in greater detail below with respect to the processes and operation to be described herein.

Referring back to the computing device 10 of FIG. 1b, the various modules (e.g., the deviation determining module 102, the template modifying module 104, and so forth) along with their sub-modules included in the computing device 10 may be implemented using hardware, software, firmware, or any combination thereof. For example, in some implementations, the deviation determining module 102 and/or the template modifying module 104 may be implemented with a processor 802 (e.g., microprocessor, controller, and so forth) executing computer readable instructions 804 (e.g., computer program product) stored in a storage medium 806 (e.g., volatile or non-volatile memory) such as a signal-bearing medium as depicted in the computing device 10 of FIG. 8. Alternatively, hardware such as application specific integrated circuit (ASIC) may be employed in order to implement such modules in some alternative implementations.

Figure 3:
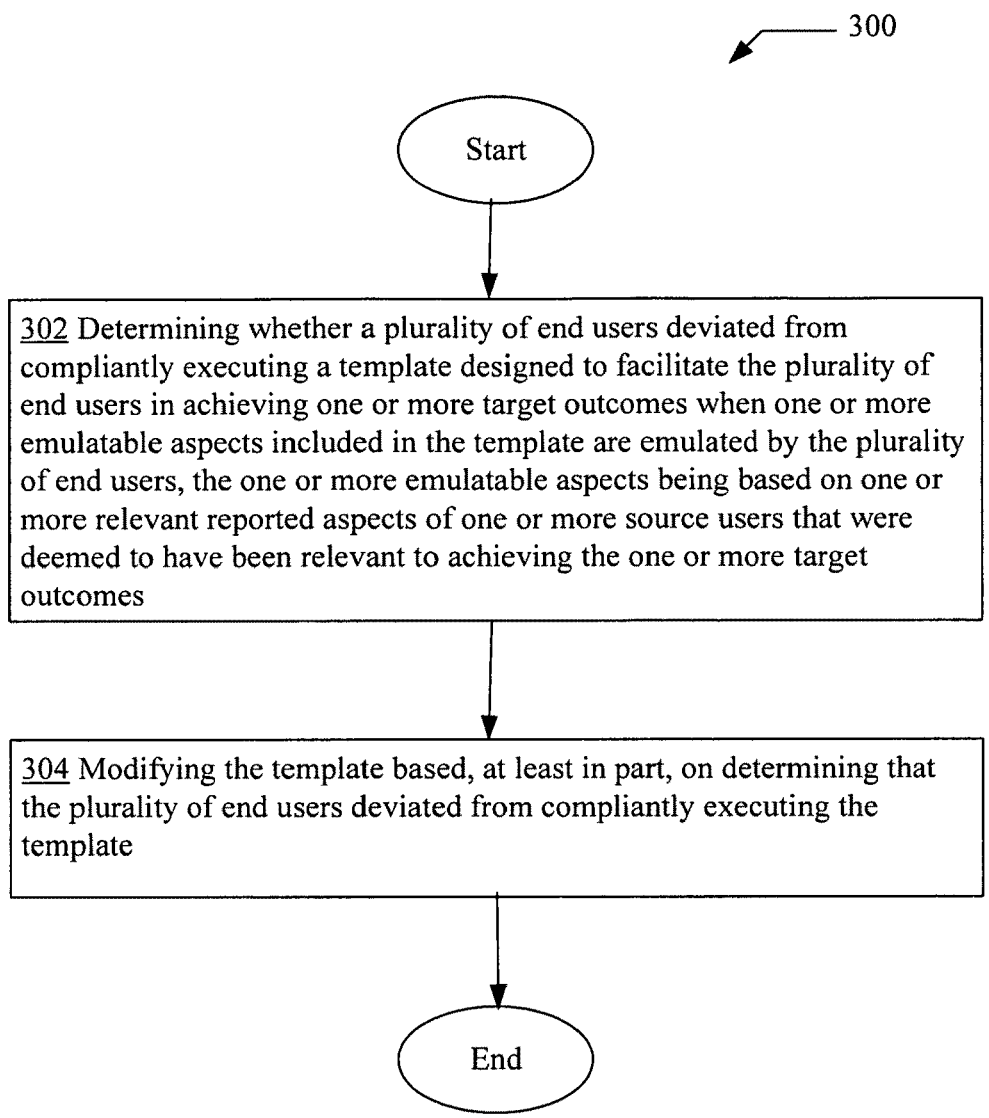
FIG. 3 is a high-level logic flowchart of a process.

A more detailed description of the computing device 10 of FIG. 1b and its components will now be provided with respect to the processes and operations to be described herein. FIG. 3 illustrates an operational flow 300 representing example operations directed to, among other things, modification of a template 16 based, at least in part, on determining whether a plurality of end users 4* deviated from compliantly executing the template 16 that is designed to facilitate the plurality of end users 4* to achieve one or more target outcomes when one or more emulatable aspects included in the template 16 or emulated. In various implementations, the plurality of end users 4* may have still achieved the one or more target outcomes associated with the template 16 even though the end users 4* may have deviated from the compliant execution of the template 16.

In FIG. 3 and in the following figures that include various examples of operational flows, discussions and explanations of the operational flows will be provided with respect to the exemplary environment 100 described above as illustrated in FIGS. 1a and 1b, and/or with respect to other examples (e.g., as provided in FIGS. 2a and 2b) and contexts. However, it should be understood that the operational flows may be executed in a number of other environments and contexts, and/or in modified versions of FIGS. 1a, 1b, 2a, and 2b. Also, although the various operational flows are presented in the sequence(s) illustrated, it should be understood that the various operations may be performed in other orders other than those which are illustrated, or may be performed concurrently.

Further, in FIG. 3 and in the figures to follow thereafter, various operations may be depicted in a box-within-a-box manner. Such depictions may indicate that an operation in an internal box may comprise an optional example embodiment of the operational step illustrated in one or more external boxes. However, it should be understood that internal box operations may be viewed as independent operations separate from any associated external boxes and may be performed in any sequence with respect to all other illustrated operations, or may be performed concurrently.

In any event, after a start operation, the operational flow 300 may move to a deviation determining operation 302 for determining whether a plurality of end users deviated from compliantly executing a template designed to facilitate the plurality of end users in achieving one or more target outcomes when one or more emulatable aspects included in the template are emulated by the plurality of end users, the one or more emulatable aspects being based on one or more relevant reported aspects of one or more source users that were deemed to have been relevant to achieving the one or more target outcomes. For instance, and as an illustration, the deviation determining module 102 of the computing device 10 of FIG. 1b determining whether a plurality of end users 4* deviated from compliantly executing a template 16 designed to facilitate the plurality of end users 4* in achieving one or more target outcomes (e.g., health or medical outcomes, user state outcomes, employment or leisure outcomes, and so forth) when one or more emulatable aspects included in the template 16 are emulated by the plurality of end users 4*, the one or more emulatable aspects being based on one or more relevant reported aspects (e.g., as indicated by source user log entries 12) of one or more source users 2* that were deemed to have been relevant to achieving the one or more target outcomes.

In addition to the deviation determining operation 302, operational flow 300 may also include a template modifying operation 304 for modifying the template based, at least in part, on determining that the plurality of end users deviated from compliantly executing the template. For instance, the template modifying module 104 of the computing device 10 modifying the template 16 based, at least in part, on determining that the plurality of end users 4* deviated from compliantly executing the template 16. In various implementations, end user data such as data obtained through end user log entries 14 that indicate reported aspects of the plurality of end users 4* may be processed in order to facilitate in the modification of the template 16. Such processing may be implemented in order to, for example, determine the type of emulatable aspects that may be included in the modified template 18. In various implementations, the deviation determining operation 302 and the template modifying operation 304 of FIG. 3 may be executed in a number of different ways.

Figure 4A:
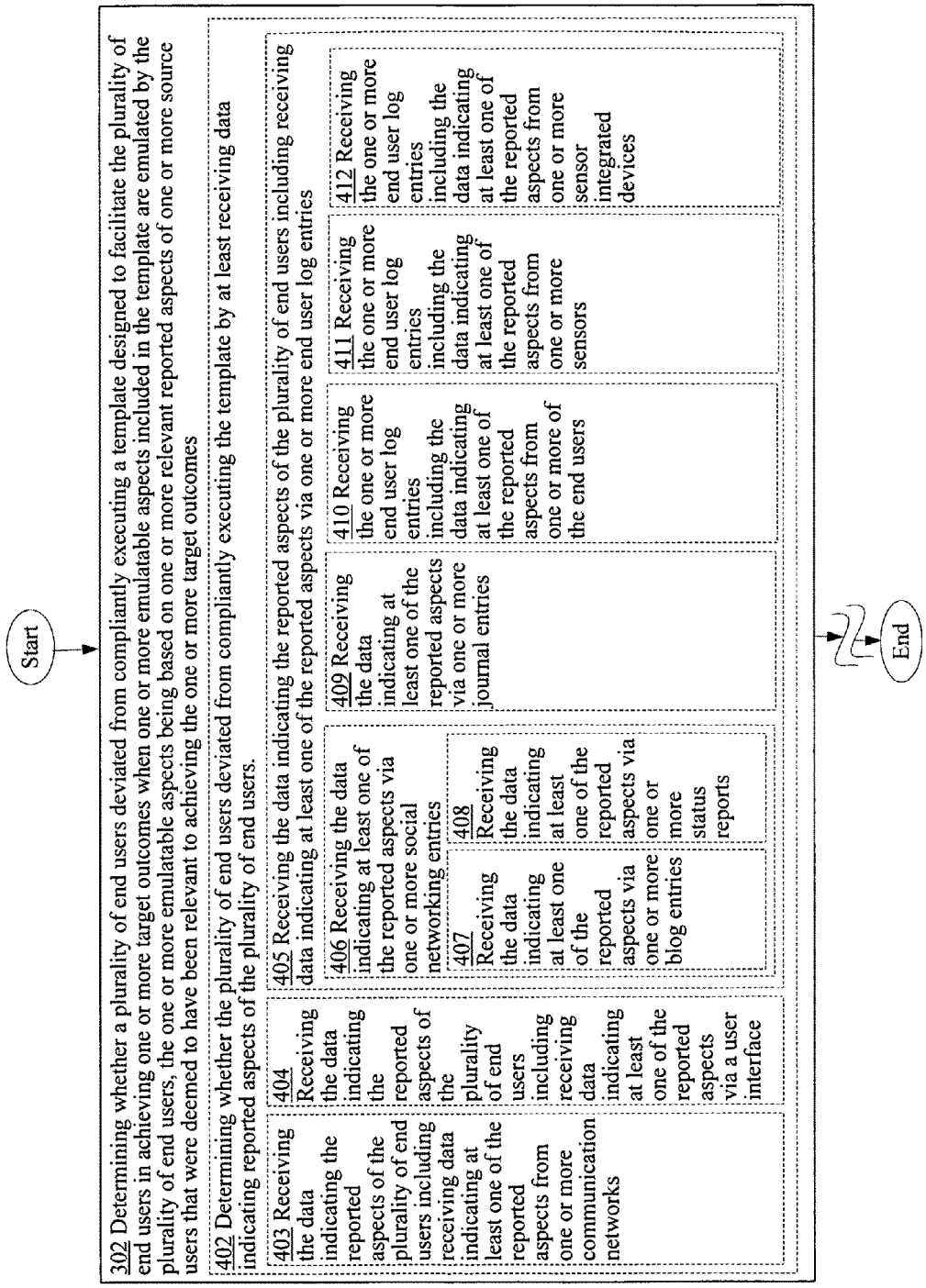
FIG. 4a is a high-level logic flowchart of a process depicting alternate implementations of the deviation determining operation 302 of FIG. 3.
Figure 4B:
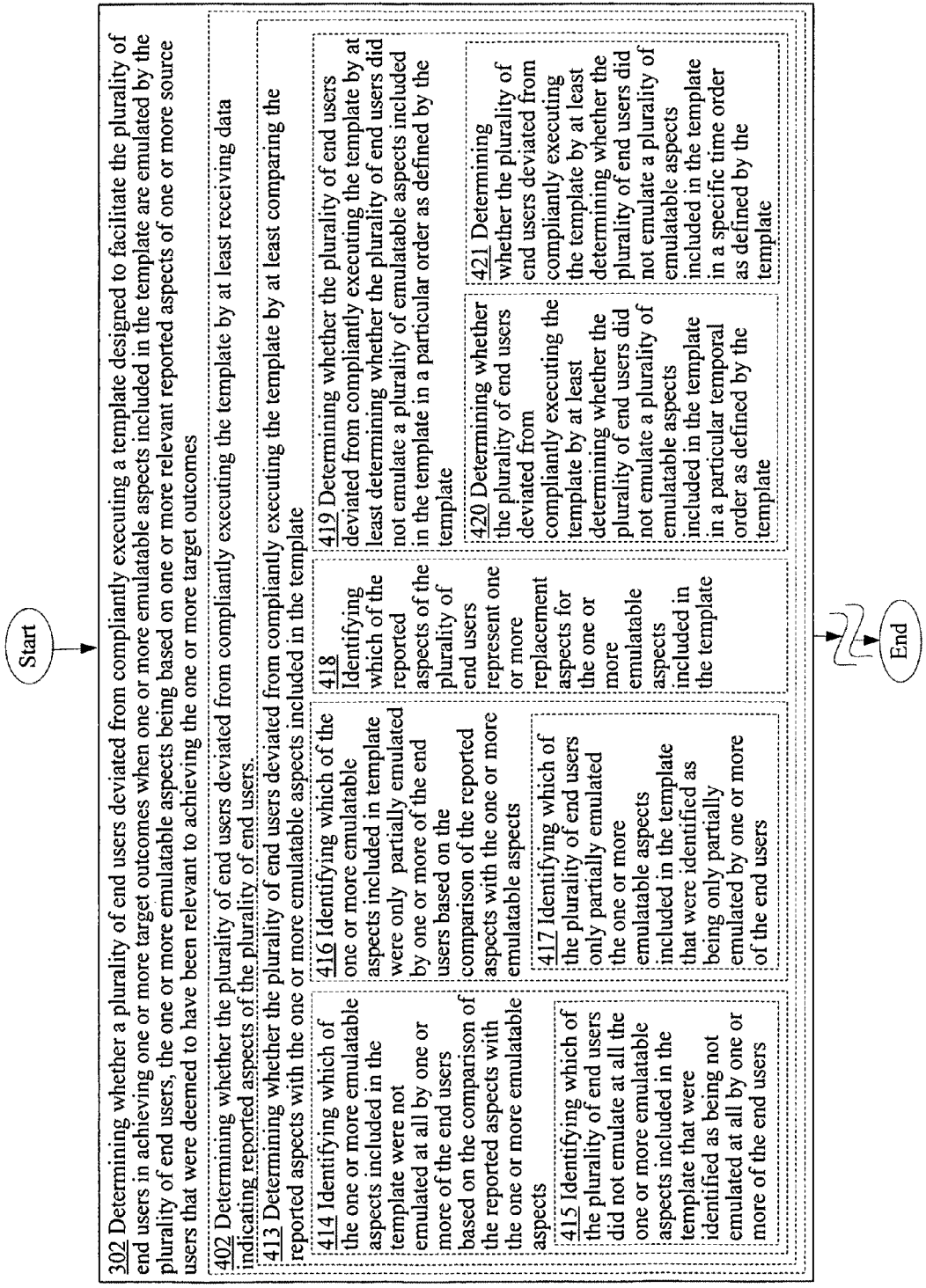
FIG. 4b is a high-level logic flowchart of a process depicting alternate implementations of the deviation determining operation 302 of FIG. 3.
Figure 4C:
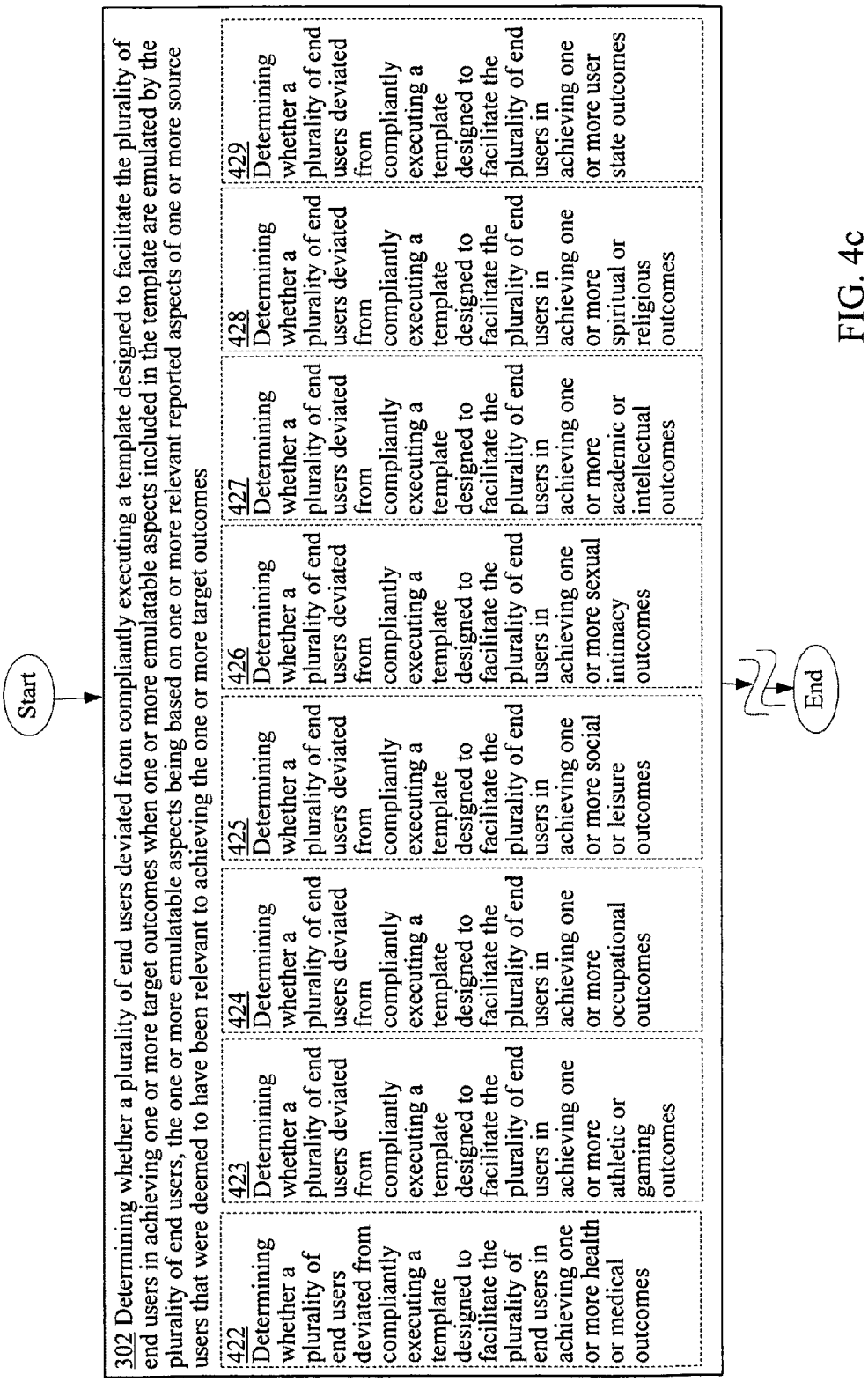
FIG. 4c is a high-level logic flowchart of a process depicting alternate implementations of the deviation determining operation 302 of FIG. 3.

For example, FIGS. 4a, 4b, and 4c illustrate various ways that the deviation determining operation 302 of FIG. 3 may be executed in various alternative implementations. For instance, the deviation from the compliant execution of the template 16 by the plurality of end users 4* to be determined through the deviation determining operation 302 may be accomplished in a variety of different ways. In some implementations, for example, the deviation determining operation 302 of FIG. 3 may include an operation 402 for determining whether the plurality of end users deviated from compliantly executing the template by at least receiving data indicating reported aspects of the plurality of end users as depicted in FIG. 4a. For instance, the deviation determining module 102 including the reported aspect data receiving module 202 (see FIG. 2a) of the computing device 10 determining whether the plurality of end users 4* deviated from compliantly executing the template 16 when the reported aspect data receiving module 202 at least receives data indicating reported aspects (e.g., dietary activities, exercise activities, mental states, medical treatment, and so forth) of the plurality of end users 4*. In some implementations, the reported aspects of the plurality of end users 4* may be the reported aspects of the end users 4* when the end users 4* were executing the template 16.

Operation 402 for receiving the data that indicates the reported aspects of the plurality of end users 4* may be executed in a number of ways. For example, in some implementations, operation 402 may include an operation 403 for receiving the data indicating the reported aspects of the plurality of end users including receiving data indicating at least one of the reported aspects from one or more communication networks as depicted in FIG. 4a. For instance, the reported aspect data receiving module 202 including the network receiving module 204 of the computing device 10 receiving the data indicating the reported aspects of the plurality of end users 4* including receiving by the network receiving module 204 of data (e.g., end user log entries 14) that indicates at least one of the reported aspects from one or more communication networks 50.

In the same or different implementations, operation 402 may include an operation 404 for receiving the data indicating the reported aspects of the plurality of end users including receiving data indicating at least one of the reported aspects via a user interface as depicted in FIG. 4a. For instance, the reported aspect data receiving module 202 including the user interface receiving module 206 of the computing device 10 when the computing device 10 is an end user device (e.g., local end user device 30*) receiving the data indicating the reported aspects of the plurality of end users 4* including receiving by the user interface receiving module 206 of data indicating at least one of the reported aspects via a user interface 120 (e.g., a keyboard or keypad, a microphone, a mouse, a touchscreen, and so forth).

In the same or different implementations, operation 402 may include an operation 405 for receiving the data indicating the reported aspects of the plurality of end users including receiving data indicating at least one of the reported aspects via one or more end user log entries as depicted in FIG. 4a. For instance, the reported aspect data receiving module 202 including the log entry receiving module 208 of the computing device 10 receiving the data indicating the reported aspects of the plurality of end users 4* including receiving by the log entry receiving module 208 of data indicating at least one of the reported aspects via one or more end user log entries 14.

Operation 405, in turn, may further include one or more additional operations in various alternative implementations. For example, in some implementations, operation 405 may include an operation 406 for receiving the data indicating at least one of the reported aspects via one or more social networking entries as depicted in FIG. 4a. For instance, the social networking entry receiving module 210 of the computing device 10 receiving the data indicating at least one of the reported aspects via one or more social networking entries.

In some implementations, operation 406 may further include an operation 407 for receiving the data indicating at least one of the reported aspects via one or more blog entries as depicted in FIG. 4a. For instance, the blog entry receiving module 212 of the computing device 10 receiving the data indicating at least one of the reported aspects via one or more blog entries (e.g., microblog entries).

In the same or different implementations, operation 406 may include an operation 408 for receiving the data indicating at least one of the reported aspects via one or more status reports as depicted in FIG. 4a. For instance, the status report receiving module 114 of the computing device 10 receiving the data indicating at least one of the reported aspects via one or more (social networking) status reports.

In some implementations, operation 405 for receiving the data indicating at least one of the reported aspects via one or more end user log entries may include an operation 409 for receiving the data indicating at least one of the reported aspects via one or more journal entries as depicted in FIG. 4a. For instance, the journal entry receiving module 216 of the computing device 10 receiving the one or more end user log entries 14 including the journal entry receiving module 216 receiving the data indicating at least one of the reported aspects via one or more journal entries.

In the same or different implementations, operation 405 may include an operation 410 for receiving the one or more end user log entries including the data indicating at least one of the reported aspects from one or more of the end users as depicted in FIG. 4a. For instance, the log entry receiving module 208 of the computing device 10 receiving (e.g., receiving via one or more communication networks 50 the one or more end user log entries 14 including the data indicating at least one of the reported aspects from one or more of the end users 4*.

In the same or different implementations, operation 405 may include an operation 411 for receiving the one or more end user log entries including the data indicating at least one of the reported aspects from one or more sensors as depicted in FIG. 4a. For instance, the log entry receiving module 208 of the computing device 10 receiving the one or more end user log entries 14 including the data indicating at least one of the reported aspects from one or more sensors 140.

In the same or different implementations, operation 405 may include an operation 412 for receiving the one or more end user log entries including the data indicating at least one of the reported aspects from one or more sensor integrated devices as depicted in FIG. 4a. For instance, the log entry receiving module 208 of the computing device 10 receiving the one or more end user log entries 14 including the data indicating at least one of the reported aspects from one or more sensor integrated devices 40 (e.g., an automobile, a treadmill, a household appliance, and so forth).

In various implementations, the operation 402 for determining whether the plurality of end users 4* deviated from compliantly executing the template 16 by at least receiving data indicating reported aspects of the plurality of end users may include an operation 413 for determining whether the plurality of end users deviated from compliantly executing the template by at least comparing the reported aspects with the one or more emulatable aspects included in the template as depicted in FIG. 4b. For instance, the deviation determining module 102 including the comparing module 218 determining whether the plurality of end users 4*deviated from compliantly executing the template 16 when the comparing module 218 at least compares the reported aspects with the one or more emulatable aspects included in the template 16.

As further illustrated in FIG. 4b, operation 413 may include one or more additional operations in various alternative implementations. For example, in some implementations, operation 413 may include an operation 414 for identifying which of the one or more emulatable aspects included in the template were not emulated at all by one or more of the end users based on the comparison of the reported aspects with the one or more emulatable aspects as depicted in FIG. 4b. For instance, the emulatable aspect identifying module 220 of the computing device 10 identifying (e.g., determining, or finding) which of the one or more emulatable aspects included in the template 16 were not emulated at all by one or more of the end users 4* based on the comparison of the reported aspects with the one or more emulatable aspects. In some cases, by making such identification, a determination may be made as to which of the one or more emulatable aspects included in the template 16 may need to be modified. Note that the phrase "at all" as used above in reference to the emulatable aspects in the template 16 that were not emulated at all indicate that these emulatable aspects were not even partially emulated by one or more end users 4* but were, for example, completely ignored or disregarded.

In some cases, operation 414 may further include an operation 415 for identifying which of the plurality of end users did not emulate at all the one or more emulatable aspects included in the template that were identified as being not emulated at all by one or more of the end users as depicted in FIG. 4b. For instance, the end user identifying module 222 of the computing device 10 identifying which of the plurality of end users 4* did not emulate at all those emulatable aspects included in the template 16 that were identified as being not emulated at all by one or more of the end users 4*. In some implementations, by making such identification, a determination may be made as to whether the template 16 should be modified. For example, in some cases, template 16 may be modified only if a majority of end users 4* or at least a significant portion of the end user 4* were identified as not emulating at all one, some, or all of the one or more emulatable aspects of the template 16.

In various implementations, operation 413 may include an operation 416 for identifying which of the one or more emulatable aspects included in template were only partially emulated by one or more of the end users based on the comparison of the reported aspects with the one or more emulatable aspects as depicted in FIG. 4b. For instance, the emulatable aspect identifying module 220 of the computing device 10 identifying which of the one or more emulatable aspects included in template 16 were only partially emulated by one or more of the end users 4* based on the comparison of the reported aspects with the one or more emulatable aspects. In some cases, by making such an identification, a determination may be made as to which of the one or more emulatable aspects included in the template 16 may need to be modified.

In some implementations, operation 416 may further include an operation 417 for identifying which of the plurality of end users only partially emulated the one or more emulatable aspects included in the template that were identified as being only partially emulated by one or more of the end users as depicted in FIG. 4b. For instance, the end user identifying module 222 of the computing device 10 identifying which of the plurality of end users 4\* only partially emulated those emulatable aspects included in the template 16 that were identified as being only partially emulated by one or more of the end users 4\*. In some implementations, by making such identification, a determination may be made as to whether the template 16 should be modified. For example, in some cases template 16 may be modified only if a majority of end users 4\* or at least a significant portion of the plurality of end users 4\* were identified as only partially emulating one, some, or all of the one or more emulatable aspects of the template 16.

In some implementations, operation 413 may include an operation 418 for identifying which of the reported aspects of the plurality of end users represent one or more replacement aspects for the one or more emulatable aspects included in the template as depicted in FIG. 4b. For instance, the reported aspect identifying module 224 of the computing device 10 identifying which of the reported aspects of the plurality of end users 4\* represent one or more replacement aspects for the one or more emulatable aspects included in the template 16 that may be replaced or revised when the template 16 is being, for example, modified. The identification of one or more replacement aspects from the reported aspects of the plurality of end users 4\* may be based on a number of factors. For example, in some implementations, reported aspects that are deviations from the one or more emulatable aspects included in the template 16 and that are most commonly executed by the end users 4\* may be identified as replacement aspects. Suppose, for example, template 16 included an emulatable aspect that required end users 4\* to go jogging for 30 minutes on the fourth day. However, if most of the non-compliant end users 4\* went swimming 20 minutes on the fourth day rather than jogging, than swimming for 20 minutes may be identified as a replacement aspect.

In same or different implementations, operation 413 may include an operation 419 for determining whether the plurality of end users deviated from compliantly executing the template by at least determining whether the plurality of end users did not emulate a plurality of emulatable aspects included in the template in a particular order as defined by the template as depicted in FIG. 4b. For instance, the deviation determining module 102 including the particular order determining module 226 of the computing device 10 determining whether the plurality of end users 4\* deviated from compliantly executing the template 16 when the particular order determining module 226 at least determines whether the plurality of end users 4\* did not emulate a plurality of emulatable aspects included in the template 16 in a particular order as defined by the template 16. In other words, if the template 16 includes a plurality of emulatable aspects, and the template 16 defines the temporal or specific time order in which the emulatable aspects are to be emulated, than an end user 4\* may not have compliantly executed the template 16 if the end user 4\* emulates at least some of the emulatable aspects in an incorrect order (e.g., incorrect sequence).

In various implementations, operation 419 may further include an operation 420 for determining whether the plurality of end users deviated from compliantly executing the template by at least determining whether the plurality of end users did not emulate a plurality of emulatable aspects included in the template in a particular temporal order as defined by the template as depicted in FIG. 4b. For instance, the deviation determining module 102 including the particular order determining module 226 of the computing device 10 determining whether the plurality of end users 4\* deviated from compliantly executing the template 16 when the particular order determining module 226 at least determines whether the plurality of end users 4\* did not emulate a plurality of emulatable aspects included in the template 16 in a particular temporal order as defined by the template 16.

In some implementations, operation 419 may include an operation 421 for determining whether the plurality of end users deviated from compliantly executing the template by at least determining whether the plurality of end users did not emulate a plurality of emulatable aspects included in the template in a specific time order as defined by the template as depicted in FIG. 4b. For instance, the deviation determining module 102 including the particular order determining module 226 of the computing device 10 determining whether the plurality of end users 4\* deviated from compliantly executing the template 16 when the particular order determining module 226 at least determines whether the plurality of end users 4\* did not emulate a plurality of emulatable aspects included in the template 16 in a specific time order as defined by the template 16.

Various types of templates 16 may be involved in the deviation determining operation 302 of FIG. 3. For example, in some implementations, the deviation determining operation 302 may include an operation 422 for determining whether a plurality of end users deviated from compliantly executing a template designed to facilitate the plurality of end users in achieving one or more health or medical outcomes as depicted in FIG. 4c. For instance, the deviation determining module 102 of the computing device 10 determining whether a plurality of end users 4\* deviated from compliantly executing a template 16 designed to facilitate the plurality of end users 4\* in achieving one or more health or medical outcomes (e.g., losing weight, improve results of a medical treatment, reduce pain, reduce stress, reduce blood pressure or blood glucose levels, and so forth).

In some implementations, the deviation determining operation 302 may include an operation 423 for determining whether a plurality of end users deviated from compliantly executing a template designed to facilitate the plurality of end users in achieving one or more athletic or gaming outcomes as depicted in FIG. 4c. For instance, the deviation determining module 102 of the computing device 10 determining whether a plurality of end users 4\* deviated from compliantly executing a template 16 designed to facilitate the plurality of end users 4\* in achieving one or more athletic or gaming outcomes (e.g., win a tennis tournament, lower golf handicap, improve scores on an electronic game, and so forth).

In some implementations, the deviation determining operation 302 may include an operation 424 for determining whether a plurality of end users deviated from compliantly executing a template designed to facilitate the plurality of end users in achieving one or more occupational outcomes as depicted in FIG. 4c. For instance, the deviation determining module 102 of the computing device 10 determining whether a plurality of end users 4\* deviated from compliantly executing a template 16 designed to facilitate the plurality of end users 4\* in achieving one or more occupational outcomes (e.g., be promoted, develop business network, complete a project, and so forth).

In some implementations, the deviation determining operation 302 may include an operation 425 for determining whether a plurality of end users deviated from compliantly executing a template designed to facilitate the plurality of end users in achieving one or more social or leisure outcomes as depicted in FIG. 4c. For instance, the deviation determining module 102 of the computing device 10 determining whether a plurality of end users 4* deviated from compliantly executing a template 16 designed to facilitate the plurality of end users 4* in achieving one or more social or leisure outcomes (e.g., develop more friendships, achieve certain social status, be invited to join a particular social club, and so forth).

In some implementations, the deviation determining operation 302 may include an operation 426 for determining whether a plurality of end users deviated from compliantly executing a template designed to facilitate the plurality of end users in achieving one or more sexual intimacy outcomes as depicted in FIG. 4c. For instance, the deviation determining module 102 of the computing device 10 determining whether a plurality of end users 4* deviated from compliantly executing a template 16 designed to facilitate the plurality of end users 4* in achieving one or more sexual intimacy outcomes (e.g., increase the frequency of sexual encounters).

In some implementations, the deviation determining operation 302 may include an operation 427 for determining whether a plurality of end users deviated from compliantly executing a template designed to facilitate the plurality of end users in achieving one or more academic or intellectual outcomes as depicted in FIG. 4c. For instance, the deviation determining module 102 of the computing device 10 determining whether a plurality of end users 4* deviated from compliantly executing a template 16 designed to facilitate the plurality of end users 4* in achieving one or more academic or intellectual outcomes (e.g., understanding particular concepts introduced in a book, accepted for enrollment at a particular University, and so forth).

In some implementations, the deviation determining operation 302 may include an operation 428 for determining whether a plurality of end users deviated from compliantly executing a template designed to facilitate the plurality of end users in achieving one or more spiritual or religious outcomes as depicted in FIG. 4c. For instance, the deviation determining module 102 of the computing device 10 determining whether a plurality of end users 4* deviated from compliantly executing a template 16 designed to facilitate the plurality of end users 4* in achieving one or more spiritual or religious outcomes (e.g., achieve spiritual harmony, acceptance to a particular church or religion, and so forth).

In some implementations, the deviation determining operation 302 may include an operation 429 for determining whether a plurality of end users deviated from compliantly executing a template designed to facilitate the plurality of end users in achieving one or more user state outcomes as depicted in FIG. 4c. For instance, the deviation determining module 102 of the computing device 10 determining whether a plurality of end users 4* deviated from compliantly executing a template 16 designed to facilitate the plurality of end users 4* in achieving one or more user state outcomes (e.g., achieve certain subjective user states such as being "happy" or "content," achieve certain social states such as being married, and so forth).

Figure 5A:
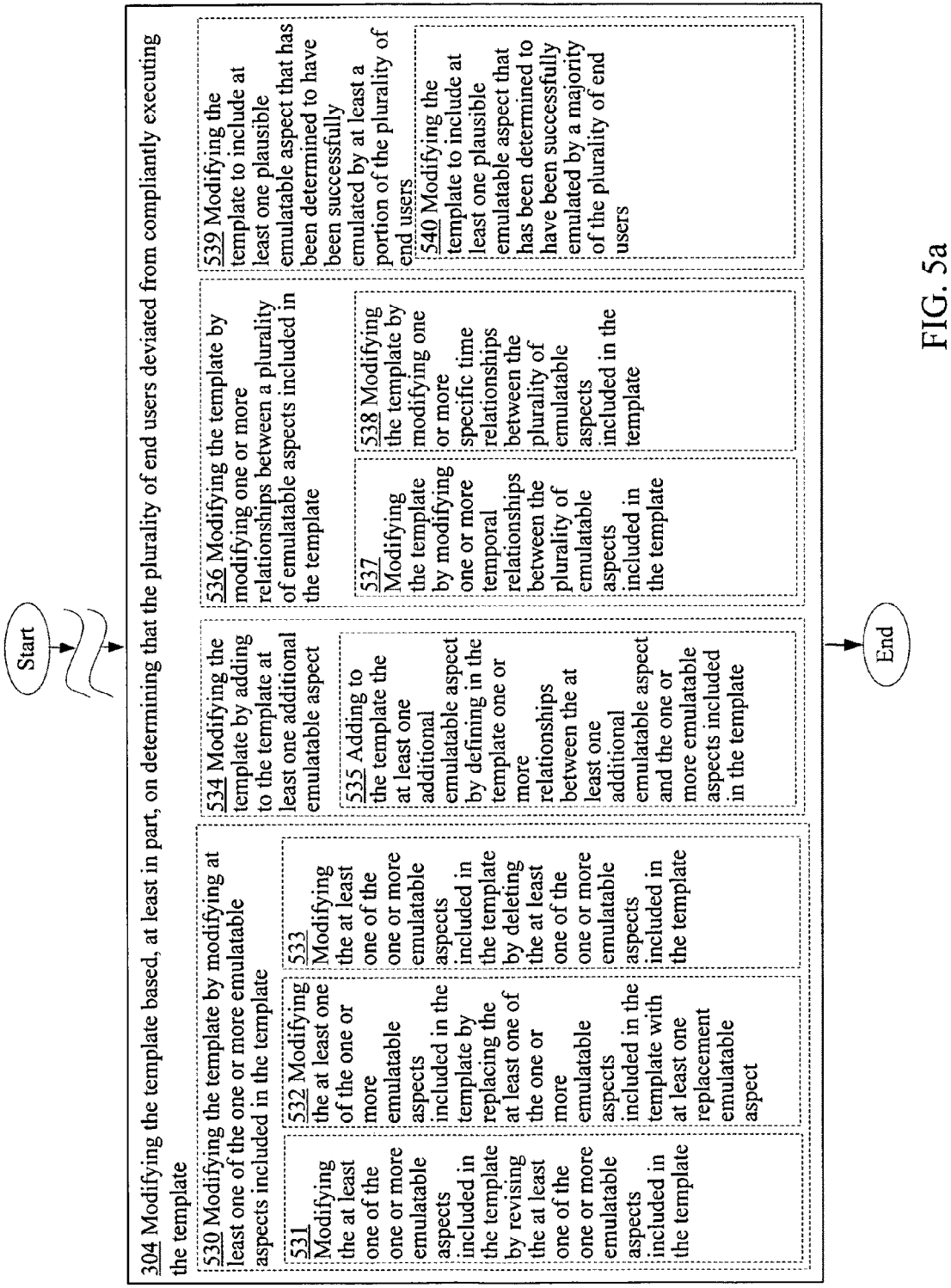
FIG. 5a is a high-level logic flowchart of a process depicting alternate implementations of the particular template modifying operation 304 of FIG. 3.

Referring back to FIG. 3, the template modifying operation 304 may be implemented in a number of different ways in various alternative implementations. For example, in some implementations, the template modifying operation 304 of FIG. 3 may include an operation 530 for modifying the template by modifying at least one of the one or more emulatable aspects included in the template as depicted in FIG. 5a. For instance, the template modifying module 104 including the emulatable aspect modifying module 230 of the computing device 10 modifying the template 16 when the emulatable aspect modifying module 230 modifies at least one of the one or more emulatable aspects included in the template 16.

There are a number of ways in which an emulatable aspect that may be included in a template 16 may be modified. For example, in some implementations, operation 530 may include an operation 531 for modifying the at least one of the one or more emulatable aspects included in the template by revising the at least one of the one or more emulatable aspects included in the template as depicted in FIG. 5a. For instance, the emulatable aspect modifying module 230 including the emulatable aspect revising module 232 modifying the at least one of the one or more emulatable aspects included in the template 16 when the emulatable aspect revising module 232 revises the at least one of the one or more emulatable aspects included in the template 16.

In the same or different implementations, operation 530 may include an operation 532 for modifying the at least one of the one or more emulatable aspects included in the template by replacing the at least one of the one or more emulatable aspects included in the template with at least one replacement emulatable aspect as depicted in FIG. 5a. For instance, the emulatable aspect modifying module 230 including the emulatable aspect replacing module 234 modifying the at least one of the one or more emulatable aspects included in the template 16 when the emulatable aspect replacing module 234 replaces the at least one of the one or more emulatable aspects included in the template 16 with at least one replacement emulatable aspect.

In the same or different implementations, operation 530 may include an operation 533 for modifying the at least one of the one or more emulatable aspects included in the template by deleting the at least one of the one or more emulatable aspects included in the template as depicted in FIG. 5a. For instance, the emulatable aspect modifying module 230 including the emulatable aspect deleting module 236 modifying the at least one of the one or more emulatable aspects included in the template 16 when the emulatable aspect deleting module 236 deletes the at least one of the one or more emulatable aspects included in the template 16. Note that a deletion of an emulatable aspect may be possible when, for example, it is determined that end users 4* when executing the template 16 may have skipped emulating a particular emulatable aspect included in the template 16 without compromising the outcome (e.g., achieving the target outcome).

In various implementations, the template modifying operation 304 may include an operation 534 for modifying the template by adding to the template at least one additional emulatable aspect as depicted in FIG. 5a. For instance, the template modifying module 104 including the emulatable aspect adding module 238 of the computing device 10 modifying the template 16 when the emulatable aspect adding module 238 adds to the template 16 at least one additional emulatable aspect. This may be possible, for example, when end users 4* deviate from the compliant execution of the template 16 that results in the need for an additional emulatable aspect in order to achieve the one or more target outcomes. For example, if end users 4* deviate from the compliant execution of the template 16 by swimming for only 20 minutes rather than swimming for 40 minutes as required by the template 16, then the template 16 may be modified to include an additional emulatable aspect for another 20 minute swim.

In some implementations, operation 534 may further include an operation 535 for adding to the template the at least one additional emulatable aspect by defining in the template one or more relationships between the at least one additional emulatable aspect and the one or more emulatable aspects included in the template as depicted in FIG. 5a. For instance, the emulatable aspect adding module 238 including the relationship defining module 240 of the computing device 10 adding to the template 16 the at least one additional emulatable aspect including defining by the relationship defining module 240 in the template 16 one or more relationships (e.g., temporal or specific time relationships) between the at least one additional emulatable aspect and the one or more emulatable aspects included in the template 16.

In the same or different implementations, the template modifying operation 304 may include an operation 536 for modifying the template by modifying one or more relationships between a plurality of emulatable aspects included in the template as depicted in FIG. 5a. For instance, the template modifying module 104 including the relationship modifying module 242 modifying the template 16 including modifying by the relationship modifying module 242 one or more relationships between a plurality of emulatable aspects included in the template 16.

In various implementations, operation 536 may further include an operation 537 for modifying the template by modifying one or more temporal relationships between the plurality of emulatable aspects included in the template as depicted in FIG. 5a. For instance, the template modifying module 104 including the relationship modifying module 242 modifying the template 16 including modifying by the relationship modifying module 242 one or more temporal relationships between a plurality of emulatable aspects included in the template 16.

In some implementations, operation 536 may include an operation 538 for modifying the template by modifying one or more specific time relationships between the plurality of emulatable aspects included in the template as depicted in FIG. 5a. For instance, the template modifying module 104 including the relationship modifying module 242 modifying the template 16 including modifying by the relationship modifying module 242 one or more specific time relationships between a plurality of emulatable aspects included in the template 16.

In the same or different implementations, the template modifying operation 304 may include an operation 539 for modifying the template to include at least one plausible emulatable aspect that has been determined to have been successfully emulated by at least a portion of the plurality of end users as depicted in FIG. 5a. For instance, the template modifying module 104 of the computing device 10 modifying the template 16 to include at least one plausible emulatable aspect (e.g., a plausible modified emulatable aspect, a plausible replacement emulatable aspect, a plausible additional emulatable aspect, and so forth) that has been determined to have been successfully emulated by at least a portion of the plurality of end users 4*.

In some implementations, operation 539 for presenting one or more recommendations may include an operation 540 for modifying the template to include at least one plausible emulatable aspect that has been determined to have been successfully emulated by a majority of the plurality of end users as depicted in FIG. 5a. For instance, the template modifying module 104 of the computing device 10 modifying the template 16 to include at least one plausible emulatable aspect (e.g., a plausible modified emulatable aspect, a plausible replacement emulatable aspect, a plausible additional emulatable aspect, and so forth) that has been determined to have been successfully emulated by a majority of the plurality of end users 4*.

Figure 5B:
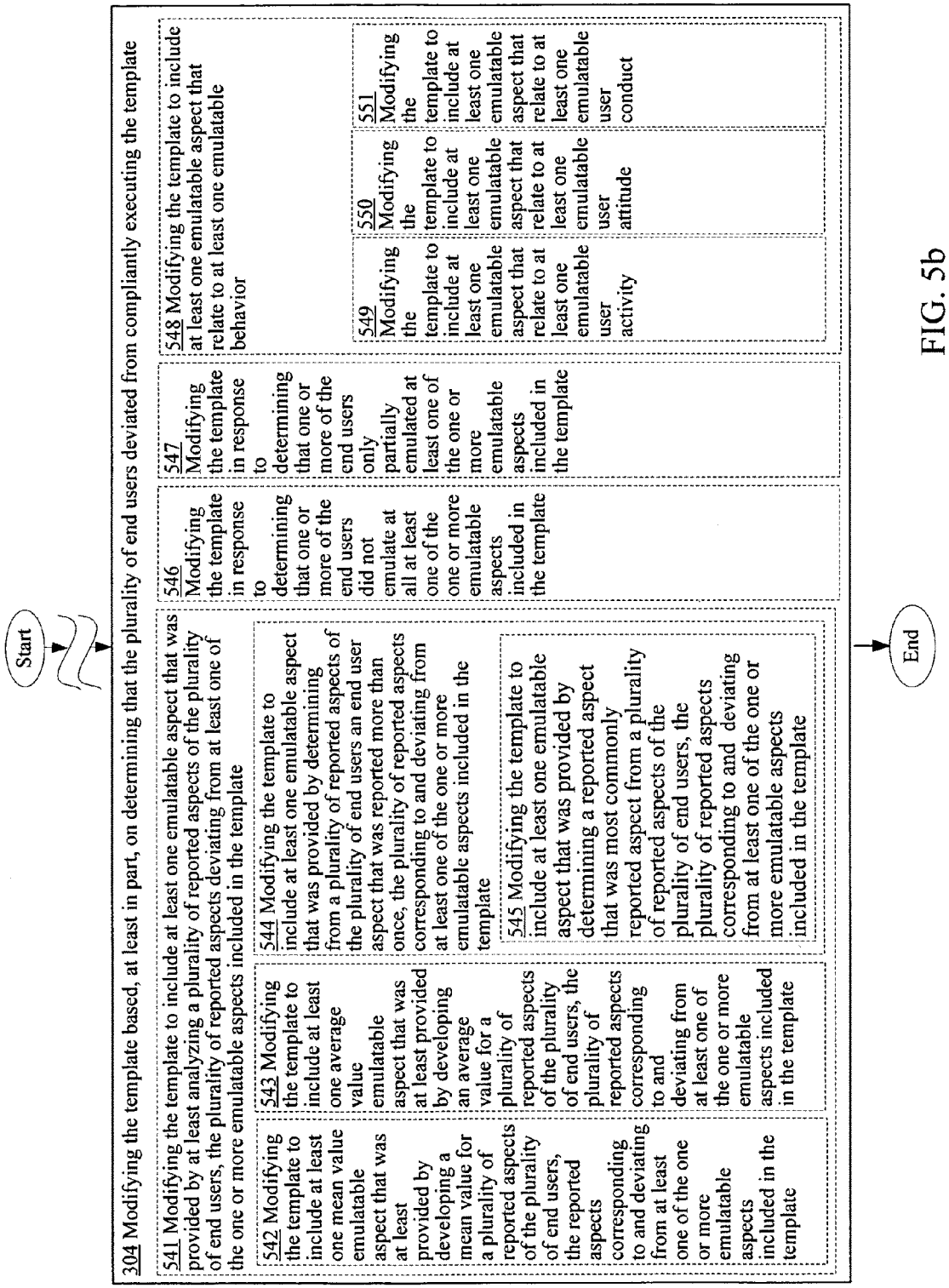
FIG. 5b is a high-level logic flowchart of a process depicting alternate implementations of the particular template modifying operation 304 of FIG. 3.

In various implementations, the one or more actions executed in the template modifying operation 304 of FIG. 3 may include an operation 541 for modifying the template to include at least one emulatable aspect that was provided by at least analyzing a plurality of reported aspects of the plurality of end users, the plurality of reported aspects deviating from at least one of the one or more emulatable aspects included in the template as depicted in FIG. 5b. For instance, the template modifying module 104 including the reported aspect analyzing module 243 modifying the template 16 to include at least one emulatable aspect that was provided by the reported aspect analyzing module 243 at least analyzing a plurality of reported aspects (e.g., as acquired through end user log entries 14) of the plurality of end users 4*, the plurality of reported aspects deviating from at least one of the one or more emulatable aspects included in the template 16.

Operation 541 may, in turn, include an operation 542 for modifying the template to include at least one mean value emulatable aspect that was at least provided by developing a mean value for a plurality of reported aspects of the plurality of end users, the reported aspects corresponding to and deviating from at least one of the one or more emulatable aspects included in the template as depicted in FIG. 5b. For instance, the template modifying module 104 including the mean value emulatable aspect developing module 246 of the computing device 10 modifying the template 16 to include at least one mean value emulatable aspect that was at least provided by the mean value emulatable aspect developing module 246 by developing a mean value for a plurality of reported aspects of the plurality of end users 4*, the reported aspects corresponding to and deviating from at least one of the one or more emulatable aspects included in the template 16. For example, suppose the template 16 included an emulatable aspect that required the end users 4* to study a particular reference book for one hour. However, if the end users 4* in executing the template 16 reported that they studied for less than or more than one hour as required by the template 16, then the mean value emulatable aspect, in this case, would be the mean reported aspects of the end users 4*.

In some implementations, operation 541 may include an operation 543 for modifying the template to include at least one average value emulatable aspect that was at least provided by developing an average value for a plurality of reported aspects of the plurality of end users, the plurality of reported aspects corresponding to and deviating from at least one of the one or more emulatable aspects included in the template as depicted in FIG. 5b. For instance, the template modifying module 104 including the average value emulatable aspect developing module 248 of the computing device 10 modifying the template 16 to include at least one average value emulatable aspect that was at least provided by the average value emulatable aspect developing module 248 by developing an average value for a plurality of reported aspects of the plurality of end users 4*, the plurality of reported aspects corresponding to and deviating from at least one of the one or more emulatable aspects included in the template 16.

In some implementations, operation 541 may include an operation 544 for modifying the template to include at least one emulatable aspect that was provided by determining from a plurality of reported aspects of the plurality of end users an end user aspect that was reported more than once, the plurality of reported aspects corresponding to and deviating from at least one of the one or more emulatable aspects included in the template as depicted in FIG. 5b. For instance, the template modifying module 104 including the reported aspect analyzing module 243 configured to modify the template 16 to include at least one emulatable aspect that was provided by the reported aspect analyzing module 243 when the reported aspect analyzing module 243 determines from a plurality of reported aspects of the plurality of end users an end user aspect (e.g., jogging for 40 minutes instead of one hour as required by the template 16) that was reported more than once, the plurality of reported aspects corresponding to and deviating from at least one of the one or more emulatable aspects included in the template 16. In other words, looking at the reported aspects of end users 4\* and look for deviations that occurred repeatedly. Such deviation may then be used in order to modify the template by, for example, modifying, substituting, or adding an emulatable aspect into the template 16 that corresponds to the repeated deviations.

In some implementations, operation 544 may further include an operation 545 for modifying the template to include at least one emulatable aspect that was provided by determining a reported aspect that was most commonly reported aspect from a plurality of reported aspects of the plurality of end users, the plurality of reported aspects corresponding to and deviating from at least one of the one or more emulatable aspects included in the template as depicted in FIG. 5b. For instance, the template modifying module 104 including the reported aspect analyzing module 243 configured to modify the template 16 to include at least one emulatable aspect that was provided by the reported aspect analyzing module 243 when the reported aspect analyzing module 243 determines a reported aspect that was most commonly reported aspect from a plurality of reported aspects (e.g., as indicated by end user log entries 14) of the plurality of end users 4\*, the plurality of reported aspects corresponding to and deviating from at least one of the one or more emulatable aspects included in the template. In other words, to modify the template by including into the template 16 (e.g., by substitution, modification, or addition), an emulatable aspect corresponding to the most commonly occurring deviation.

In the same or different implementations, the template modifying operation 304 of FIG. 3 may include an operation 546 for modifying the template in response to determining that one or more of the end users did not emulate at all at least one of the one or more emulatable aspects included in the template as depicted in FIG. 5b. For instance, the template modifying module 104 of the computing device 10 modifying the template 16 in response to determining that one or more of the end users 4\* did not emulate at all at least one of the one or more emulatable aspects included in the template 16.

In the same or different implementations, the template modifying operation 304 may include an operation 547 for modifying the template in response to determining that one or more of the end users only partially emulated at least one of the one or more emulatable aspects included in the template as depicted in FIG. 5b. For instance, the template modifying module 104 of the computing device 10 modifying the template 16 in response to determining that one or more of the end users 4\* only partially emulated at least one of the one or more emulatable aspects included in the template 16.

In the same or different implementations, the template modifying operation 304 may include an operation 548 for modifying the template to include at least one emulatable aspect that relate to at least one emulatable behavior as depicted in FIG. 5b. For instance, the template modifying module 104 of the computing device 10 modifying the template 16 to include (e.g., by revising, replacing, or adding) at least one emulatable aspect that relate to at least one emulatable behavior (e.g., dietary behavior, social behavior, and so forth).

In some implementations, operation 548 may include an operation 549 for modifying the template to include at least one emulatable aspect that relate to at least one emulatable user activity as depicted in FIG. 5b. For instance, the template modifying module 104 of the computing device 10 modifying the template 16 to include (e.g., by revising, replacing, or adding) at least one emulatable aspect that relate to at least one emulatable user activity (e.g., walking, resting, riding a bicycle, attending church, and so forth).

In the same or different implementations, operation 548 may include an operation 550 for modifying the template to include at least one emulatable aspect that relate to at least one emulatable user attitude as depicted in FIG. 5b. For instance, the template modifying module 104 of the computing device 10 modifying the template 16 to include (e.g., by revising, replacing, or adding) at least one emulatable aspect that relate to at least one emulatable user attitude (e.g., distaste, positive or negative attitude, and so forth).

In the same or different implementations, operation 548 may include an operation 551 for modifying the template to include at least one emulatable aspect that relate to at least one emulatable user conduct as depicted in FIG. 5b. For instance, the template modifying module 104 of the computing device 10 modifying the template 16 to include (e.g., by revising, replacing, or adding) at least one emulatable aspect that relate to at least one emulatable user conduct (e.g., treating subordinates as equals, being evasive, and so forth).

Figure 5C:
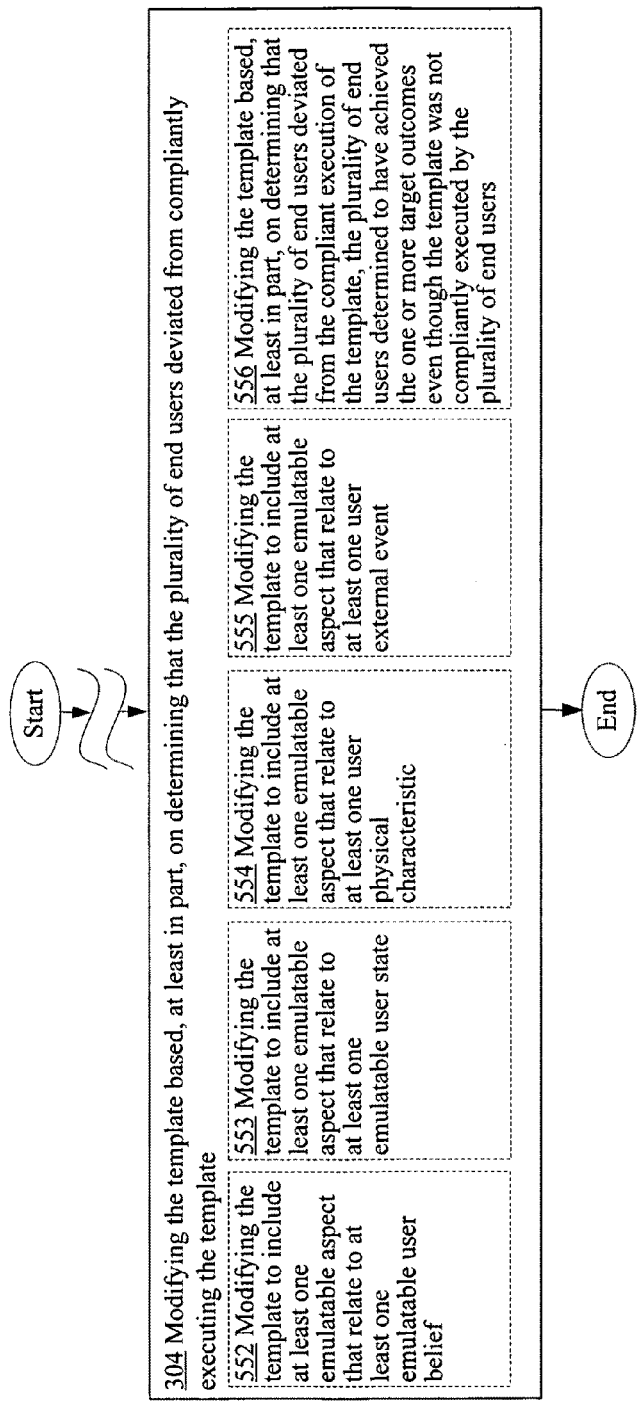
FIG. 5c is a high-level logic flowchart of a process depicting alternate implementations of the particular template modifying operation 304 of FIG. 3.

In some implementations, the template modifying operation 304 of FIG. 3 may include an operation 552 for modifying the template to include at least one emulatable aspect that relate to at least one emulatable user belief as depicted in FIG. 5c. For instance, the template modifying module 104 of the computing device 10 modifying the template 16 to include (e.g., by revising, replacing, or adding) at least one emulatable aspect that relate to at least one emulatable user belief (e.g., religious belief, spiritual belief, dietary belief, and so forth).

In the same or different implementations, the template modifying operation 304 of FIG. 3 may include an operation 553 for modifying the template to include at least one emulatable aspect that relate to at least one emulatable user state as depicted in FIG. 5c. For instance, the template modifying module 104 of the computing device 10 modifying the template 16 to include (e.g., by revising, replacing, or adding) at least one emulatable aspect that relate to at least one emulatable user state (e.g., subjective user states such as being happy, being alert, or being prepared, objective user states such as being married, being underweight, being employed, and so forth).

In the same or different implementations, the template modifying operation 304 of FIG. 3 may include an operation 554 for modifying the template to include at least one emulatable aspect that relate to at least one user physical characteristic as depicted in FIG. 5c. For instance, the template modifying module 104 of the computing device 10 modifying the template 16 to include (e.g., by revising, replacing, or adding) at least one emulatable aspect that relate to at least one user physical characteristic (e.g., low blood pressure, hair color, low body fat level, and so forth).

In the same or different implementations, the template modifying operation 304 of FIG. 3 may include an operation 555 for modifying the template to include at least one emulatable aspect that relate to at least one user external event as depicted in FIG. 5c. For instance, the template modifying module 104 of the computing device 10 modifying the template 16 to include (e.g., by revising, replacing, or adding) at least one emulatable aspect that relate to at least one user external event (e.g., local atmospheric conditions, drinking water quality, road traffic, and so forth).

In the same or different implementations, the template modifying operation 304 of FIG. 3 may include an operation 556 for modifying the template based, at least in part, on determining that the plurality of end users deviated from the compliant execution of the template, the plurality of end users determined to have achieved the one or more target outcomes even though the template was not compliantly executed by the plurality of end users as depicted in FIG. 5c. For instance, the template modifying module 104 of the computing device 10 modifying the template 16 based, at least in part, on determining that the plurality of end users 4*deviated from the compliant execution of the template 16, the plurality of end users 4* determined to have achieved the one or more target outcomes even though the template 16 was not compliantly executed by the plurality of end users 4*.

Figure 6:
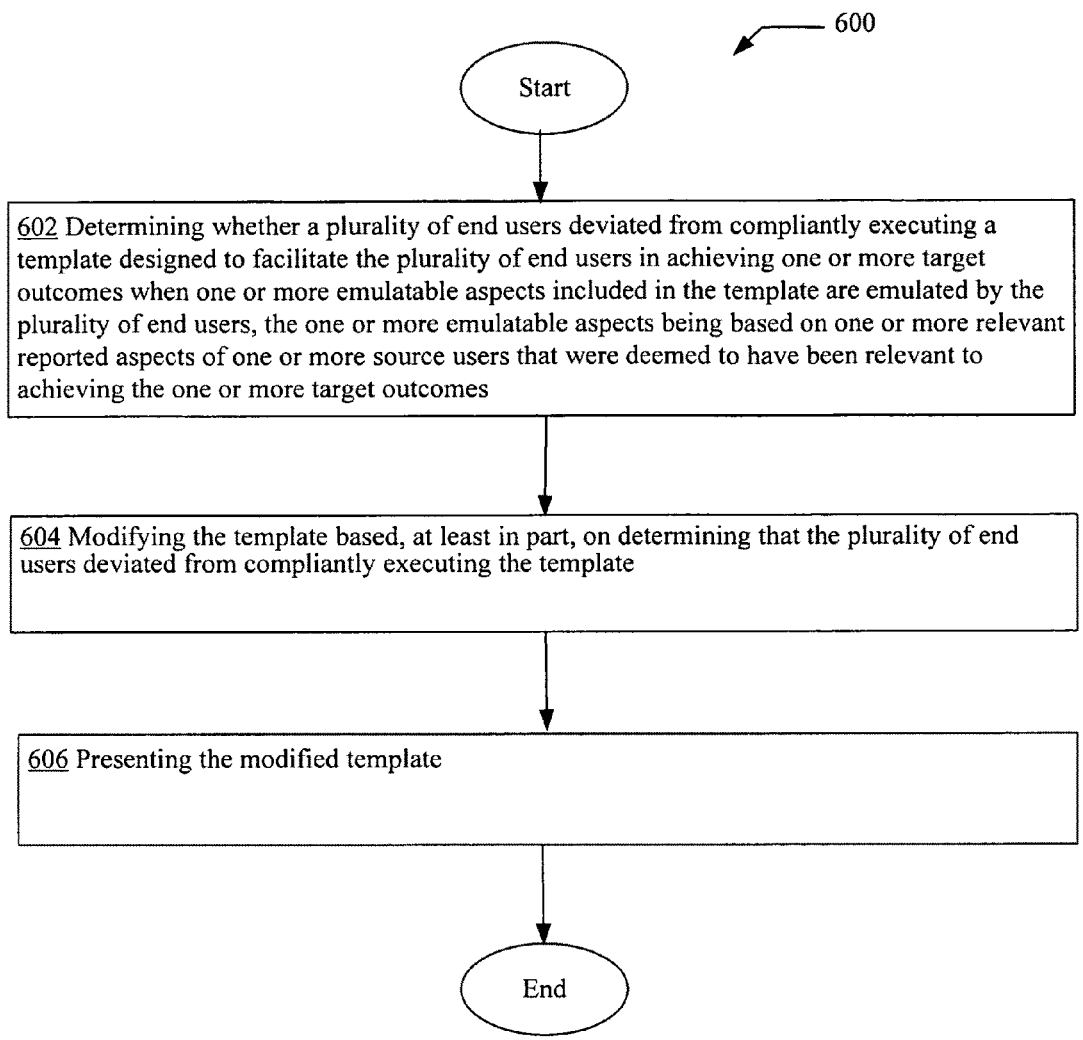
FIG. 6 is a high-level logic flowchart of another process.

Referring to FIG. 6 illustrating another operational flow 600 in accordance with various embodiments. Operational flow 600 includes certain operations that mirror the operations included in the operational flow 300 of FIG. 3. These operations include a deviation determining operation 602 and a template modifying operation 604 that corresponds to and mirror the deviation determining operation 302 and the template modifying operation 304, respectively, of FIG. 3.

In addition, operational flow 600 includes a modified template presenting operation 606 for presenting the modified template as depicted in FIG. 6. For instance, the modified template presenting module 106 of the computing device 10 presenting the modified template 18 resulting from the template modifying operation 604.

Figure 7:
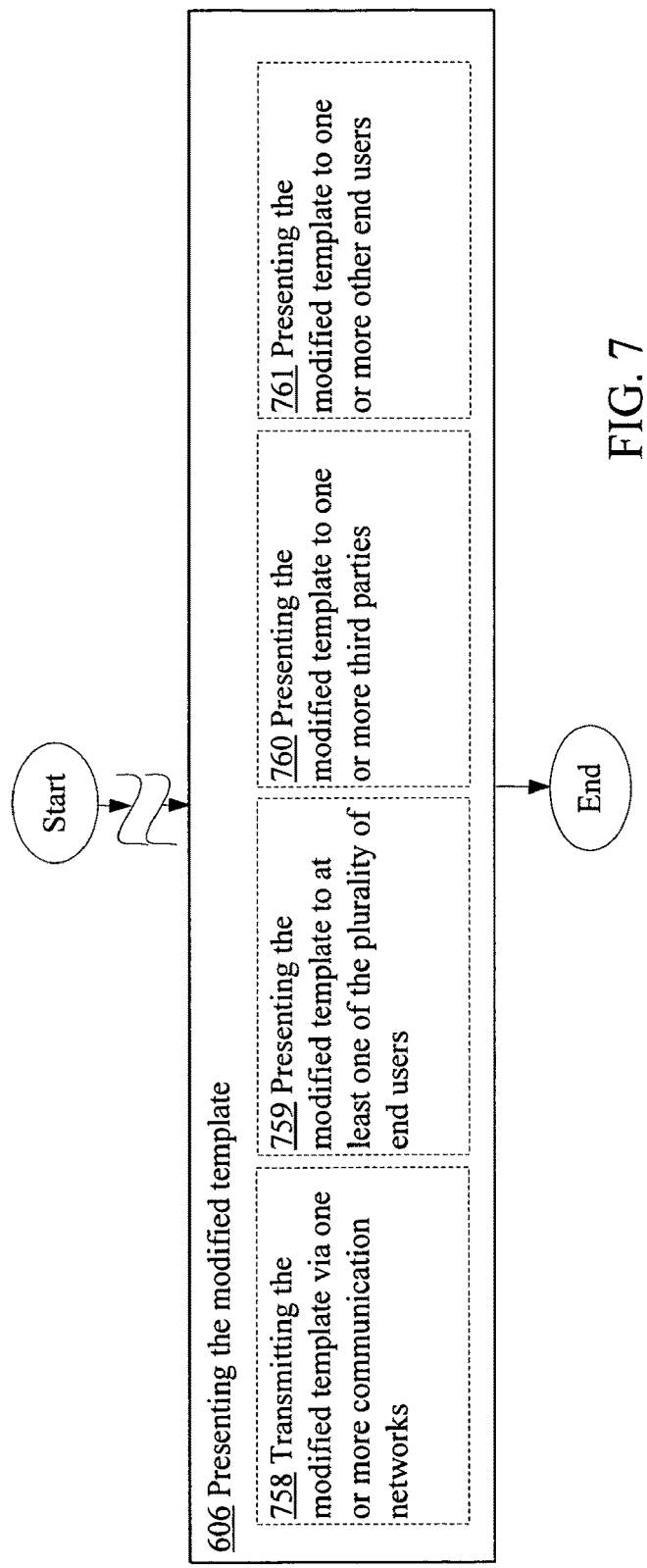
FIG. 7 is a high-level logic flowchart of a process depicting alternate implementations of the modified template presenting operation 606 of FIG. 6.

In some implementations, the modified template presenting operation 606 of FIG. 6 may include an operation 758 for transmitting the modified template via one or more communication networks as depicted in FIG. 7. For instance, the network transmitting module 130 (see FIG. 1b) of the computing device 10 transmitting the modified template 18 via one or more communication networks 50.

In the same or different implementations, the modified template presenting operation 606 of FIG. 6 may include an operation 759 for presenting the modified template to at least one of the plurality of end users as depicted in FIG. 7. For instance, the modified template presenting module 106 of the computing device 10 presenting the modified template 18 to at least one of the plurality of end users 4*.

In the same or different implementations, the modified template presenting operation 606 of FIG. 6 may include an operation 760 for presenting the modified template to one or more third parties as depicted in FIG. 7. For instance, the modified template presenting module 106 of the computing device 10 presenting the modified template 18 to one or more third parties 6 (e.g., network servers 60, content providers, and so forth).

In the same or different implementations, the modified template presenting operation 606 of FIG. 6 may include an operation 761 for presenting the modified template to one or more other end users as depicted in FIG. 7. For instance, the modified template presenting module 106 of the computing device 10 presenting the modified template 18 to one or more other end users who may have yet to execute the template 16 or the modified template 18.

Figure 8:
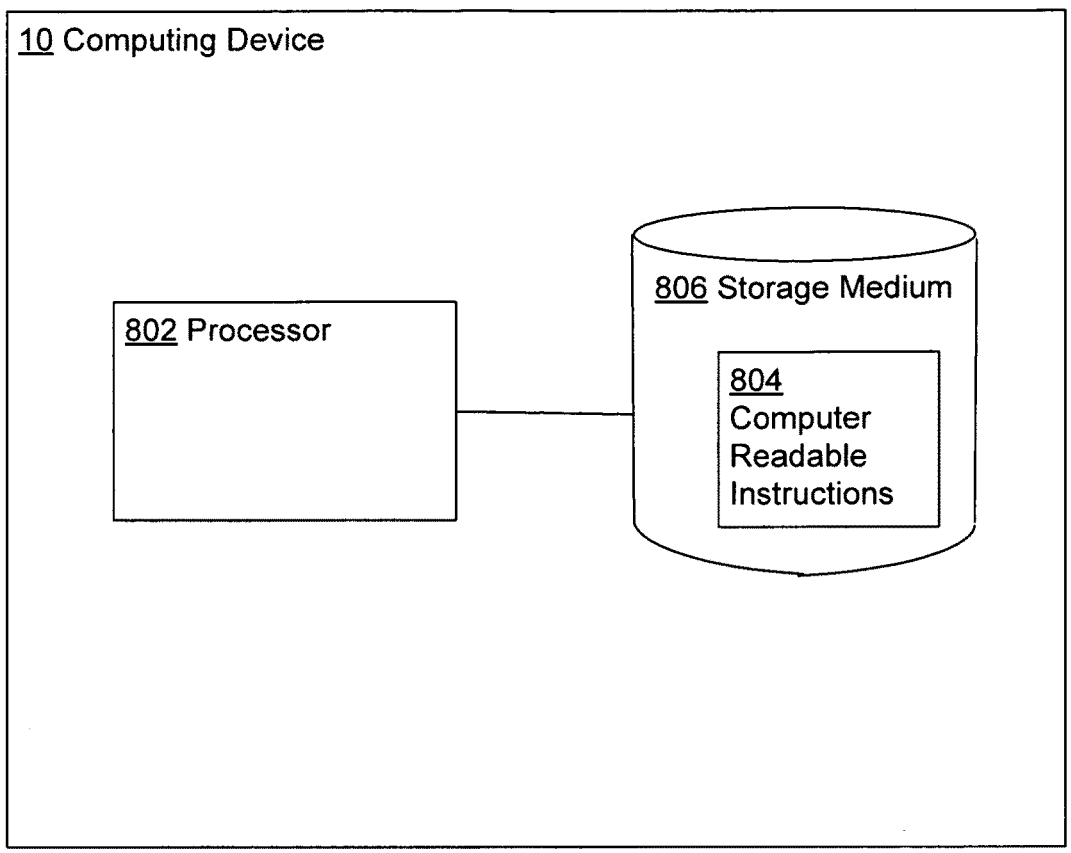
FIG. 8 is another high-level block diagram showing one implementation of the computing device 10 of FIG. 1b.

Turning now to FIG. 8, which is a high-level block diagram illustrating a particular implementation of the computing device 10 of FIG. 1b. As illustrated, the computing device 10 may include a processor 802 (e.g., microprocessor, controller, and so forth) coupled to storage medium 806 (e.g., volatile or non-volatile memory). The storage medium 806 may store computer readable instructions 804 (e.g., computer program product). The processor 802, in various implementations, may execute the computer readable instructions 804 in order to execute one or more operations described above and as illustrated in FIGS. 3, 4a, 4b, 4c, 5a, 5b, 5c, 6, and 7.

For example, the processor 802 may execute the computer readable instructions 804 in order to determine whether a plurality of end users 4* deviated from compliantly executing a template 16 designed to facilitate the plurality of end users 4* in achieving one or more target outcomes when one or more emulatable aspects included in the template 16 are emulated by the plurality of end users 4*, the one or more emulatable aspects being based on one or more relevant reported aspects of one or more source users 2* that were deemed to have been relevant to achieving the one or more target outcomes; and/or to modify the template 16 based, at least in part, on determining that the plurality of end users 4* deviated from compliantly executing the template 16 as illustrated by the operational flow 300 of FIG. 3.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuitry (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuitry, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those having skill in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A computationally-implemented system, comprising:
   means for determining whether a plurality of end users deviated from compliantly executing a template designed to facilitate the plurality of end users in achieving one or more target outcomes when one or more emulatable aspects included in the template are emulated by the plurality of end users, the one or more emulatable aspects being based on one or more relevant reported aspects of one or more source users that were deemed to have been relevant to achieving the one or more target outcomes; and
   means for modifying the template based, at least in part, on determining that the plurality of end users deviated from compliantly executing the template, wherein said means for modifying the template based, at least in part, on determining that the plurality of end users deviated from compliantly executing the template, comprises:
      means for modifying the template to include at least one plausible emulatable aspect that has been determined to have been successfully emulated by at least a portion of the plurality of end users.

2. The computationally-implemented system of claim 1, wherein said means for determining whether a plurality of end users deviated from compliantly executing a template designed to facilitate the plurality of end users in achieving one or more target outcomes when one or more emulatable aspects included in the template are emulated by the plurality of end users, the one or more emulatable aspects being based on one or more relevant reported aspects of one or more source users that were deemed to have been relevant to achieving the one or more target outcomes, comprises:
   means for determining whether the plurality of end users deviated from compliantly executing the template by at least receiving data indicating reported aspects of the plurality of end users.

3. The computationally-implemented system of claim 2, wherein said means for determining whether the plurality of end users deviated from compliantly executing the template by at least receiving data indicating reported aspects of the plurality of end users, comprises:
   means for receiving the data indicating the reported aspects of the plurality of end users including receiving data indicating at least one of the reported aspects via one or more end user log entries.

4. The computationally-implemented system of claim 3, wherein said means for receiving the data indicating the reported aspects of the plurality of end users including receiving data indicating at least one of the reported aspects via one or more end user log entries, comprises:
   means for receiving the data indicating at least one of the reported aspects via one or more social networking entries.

5. The computationally-implemented system of claim 4, wherein said means for receiving the data indicating at least one of the reported aspects via one or more social networking entries, comprises:
   means for receiving the data indicating at least one of the reported aspects via one or more blog entries.

6. The computationally-implemented system of claim 4, wherein said means for receiving the data indicating at least one of the reported aspects via one or more social networking entries, comprises:
   means for receiving the data indicating at least one of the reported aspects via one or more status reports.

7. The computationally-implemented system of claim 3, wherein said means for receiving the data indicating the reported aspects of the plurality of end users including receiving data indicating at least one of the reported aspects via one or more end user log entries, comprises:
   means for receiving the data indicating at least one of the reported aspects via one or more journal entries.

8. The computationally-implemented system of claim 3, wherein said means for receiving the data indicating the reported aspects of the plurality of end users including receiving data indicating at least one of the reported aspects via one or more end user log entries, comprises:
   means for receiving the one or more end user log entries including the data indicating at least one of the reported aspects from one or more sensors.

9. The computationally-implemented system of claim 3, wherein said means for receiving the data indicating the reported aspects of the plurality of end users including receiving data indicating at least one of the reported aspects via one or more end user log entries, comprises:
   means for receiving the one or more end user log entries including the data indicating at least one of the reported aspects from one or more sensor integrated devices.

10. The computationally-implemented system of claim 2, wherein said means for determining whether the plurality of end users deviated from compliantly executing the template by at least receiving data indicating reported aspects of the plurality of end users, comprises:
    means for determining whether the plurality of end users deviated from compliantly executing the template by at least comparing the reported aspects with the one or more emulatable aspects included in the template.

11. The computationally-implemented system of claim 10, wherein said means for determining whether the plurality of end users deviated from compliantly executing the template by at least comparing the reported aspects with the one or more emulatable aspects included in the template, comprises:
    means for identifying which of the one or more emulatable aspects included in the template were not emulated at all by one or more of the end users based on the comparison of the reported aspects with the one or more emulatable aspects.

12. The computationally-implemented system of claim 11, wherein said means for identifying which of the one or more emulatable aspects included in the template were not emulated at all by one or more of the end users based on the comparison of the reported aspects with the one or more emulatable aspects, comprises:
    means for identifying which of the plurality of end users did not emulate at all the one or more emulatable aspects included in the template that were identified as being not emulated at all by one or more of the end users.

13. The computationally-implemented system of claim 10, wherein said means for determining whether the plurality of end users deviated from compliantly executing the template by at least comparing the reported aspects with the one or more emulatable aspects included in the template, comprises:
   means for identifying which of the one or more emulatable aspects included in template were only partially emulated by one or more of the end users based on the comparison of the reported aspects with the one or more emulatable aspects.

14. The computationally-implemented system of claim 13, wherein said means for identifying which of the one or more emulatable aspects included in template were only partially emulated by one or more of the end users based on the comparison of the reported aspects with the one or more emulatable aspects, comprises:
   means for identifying which of the plurality of end users only partially emulated the one or more emulatable aspects included in the template that were identified as being only partially emulated by one or more of the end users.

15. The computationally-implemented system of claim 10, wherein said means for determining whether the plurality of end users deviated from compliantly executing the template by at least comparing the reported aspects with the one or more emulatable aspects included in the template, comprises:
   means for identifying which of the reported aspects of the plurality of end users represent one or more replacement aspects for the one or more emulatable aspects included in the template.

16. The computationally-implemented system of claim 10, wherein said means for determining whether the plurality of end users deviated from compliantly executing the template by at least comparing the reported aspects with the one or more emulatable aspects included in the template, comprises:
   means for determining whether the plurality of end users deviated from compliantly executing the template by at least determining whether the plurality of end users did not emulate a plurality of emulatable aspects included in the template in a particular order as defined by the template.

17. The computationally-implemented system of claim 16, wherein said means for determining whether the plurality of end users deviated from compliantly executing the template by at least determining whether the plurality of end users did not emulate a plurality of emulatable aspects included in the template in a particular order as defined by the template, comprises:
   means for determining whether the plurality of end users deviated from compliantly executing the template by at least determining whether the plurality of end users did not emulate a plurality of emulatable aspects included in the template in a particular temporal order as defined by the template.

18. The computationally-implemented system of claim 16, wherein said means for determining whether the plurality of end users deviated from compliantly executing the template by at least determining whether the plurality of end users did not emulate a plurality of emulatable aspects included in the template in a particular order as defined by the template, comprises:
   means for determining whether the plurality of end users deviated from compliantly executing the template by at least determining whether the plurality of end users did not emulate a plurality of emulatable aspects included in the template in a specific time order as defined by the template.

19. The computationally-implemented system of claim 1, wherein said means for determining whether a plurality of end users deviated from compliantly executing a template designed to facilitate the plurality of end users in achieving one or more target outcomes when one or more emulatable aspects included in the template are emulated by the plurality of end users, the one or more emulatable aspects being based on one or more relevant reported aspects of one or more source users that were deemed to have been relevant to achieving the one or more target outcomes, comprises:
   means for determining whether a plurality of end users deviated from compliantly executing a template designed to facilitate the plurality of end users in achieving one or more health or medical outcomes.

20. The computationally-implemented system of claim 1, wherein said means for determining whether a plurality of end users deviated from compliantly executing a template designed to facilitate the plurality of end users in achieving one or more target outcomes when one or more emulatable aspects included in the template are emulated by the plurality of end users, the one or more emulatable aspects being based on one or more relevant reported aspects of one or more source users that were deemed to have been relevant to achieving the one or more target outcomes, comprises:
   means for determining whether a plurality of end users deviated from compliantly executing a template designed to facilitate the plurality of end users in achieving one or more athletic or gaming outcomes.

21. The computationally-implemented system of claim 1, wherein said means for determining whether a plurality of end users deviated from compliantly executing a template designed to facilitate the plurality of end users in achieving one or more target outcomes when one or more emulatable aspects included in the template are emulated by the plurality of end users, the one or more emulatable aspects being based on one or more relevant reported aspects of one or more source users that were deemed to have been relevant to achieving the one or more target outcomes, comprises:
   means for determining whether a plurality of end users deviated from compliantly executing a template designed to facilitate the plurality of end users in achieving one or more occupational outcomes.

22. The computationally-implemented system of claim 1, wherein said means for determining whether a plurality of end users deviated from compliantly executing a template designed to facilitate the plurality of end users in achieving one or more target outcomes when one or more emulatable aspects included in the template are emulated by the plurality of end users, the one or more emulatable aspects being based on one or more relevant reported aspects of one or more source users that were deemed to have been relevant to achieving the one or more target outcomes, comprises:
   means for determining whether a plurality of end users deviated from compliantly executing a template designed to facilitate the plurality of end users in achieving one or more social or leisure outcomes.

23. The computationally-implemented system of claim 1, wherein said means for determining whether a plurality of end users deviated from compliantly executing a template designed to facilitate the plurality of end users in achieving one or more target outcomes when one or more emulatable aspects included in the template are emulated by the plurality of end users, the one or more emulatable aspects being based on one or more relevant reported aspects of one or more source users that were deemed to have been relevant to achieving the one or more target outcomes, comprises:

means for determining whether a plurality of end users deviated from compliantly executing a template designed to facilitate the plurality of end users in achieving one or more sexual intimacy outcomes.

24. The computationally-implemented system of claim 1, wherein said means for determining whether a plurality of end users deviated from compliantly executing a template designed to facilitate the plurality of end users in achieving one or more target outcomes when one or more emulatable aspects included in the template are emulated by the plurality of end users, the one or more emulatable aspects being based on one or more relevant reported aspects of one or more source users that were deemed to have been relevant to achieving the one or more target outcomes, comprises:

means for determining whether a plurality of end users deviated from compliantly executing a template designed to facilitate the plurality of end users in achieving one or more academic or intellectual outcomes.

25. The computationally-implemented system of claim 1, wherein said means for determining whether a plurality of end users deviated from compliantly executing a template designed to facilitate the plurality of end users in achieving one or more target outcomes when one or more emulatable aspects included in the template are emulated by the plurality of end users, the one or more emulatable aspects being based on one or more relevant reported aspects of one or more source users that were deemed to have been relevant to achieving the one or more target outcomes, comprises:

means for determining whether a plurality of end users deviated from compliantly executing a template designed to facilitate the plurality of end users in achieving one or more spiritual or religious outcomes.

26. The computationally-implemented system of claim 1, wherein said means for determining whether a plurality of end users deviated from compliantly executing a template designed to facilitate the plurality of end users in achieving one or more target outcomes when one or more emulatable aspects included in the template are emulated by the plurality of end users, the one or more emulatable aspects being based on one or more relevant reported aspects of one or more source users that were deemed to have been relevant to achieving the one or more target outcomes, comprises:

means for determining whether a plurality of end users deviated from compliantly executing a template designed to facilitate the plurality of end users in achieving one or more user state outcomes.

27. The computationally-implemented system of claim 1, wherein said means for modifying the template based, at least in part, on determining that the plurality of end users deviated from compliantly executing the template, comprises:

means for modifying the template by modifying at least one of the one or more emulatable aspects included in the template.

28. The computationally-implemented system of claim 27, wherein said means for modifying the template by modifying at least one of the one or more emulatable aspects included in the template, comprises:

means for modifying the at least one of the one or more emulatable aspects included in the template by revising the at least one of the one or more emulatable aspects included in the template.

29. The computationally-implemented system of claim 27, wherein said means for modifying the template by modifying at least one of the one or more emulatable aspects included in the template, comprises:

means for modifying the at least one of the one or more emulatable aspects included in the template by replacing the at least one of the one or more emulatable aspects included in the template with at least one replacement emulatable aspect.

30. The computationally-implemented system of claim 27, wherein said means for modifying the template by modifying at least one of the one or more emulatable aspects included in the template, comprises:

means for modifying the at least one of the one or more emulatable aspects included in the template by deleting the at least one of the one or more emulatable aspects included in the template.

31. The computationally-implemented system of claim 1, wherein said means for modifying the template based, at least in part, on determining that the plurality of end users deviated from compliantly executing the template, comprises:

means for modifying the template by adding to the template at least one additional emulatable aspect.

32. The computationally-implemented system of claim 31, wherein said means for modifying the template by adding to the template at least one additional emulatable aspect, comprises:

means for adding to the template the at least one additional emulatable aspect by defining in the template one or more relationships between the at least one additional emulatable aspect and the one or more emulatable aspects included in the template.

33. The computationally-implemented system of claim 1, wherein said means for modifying the template based, at least in part, on determining that the plurality of end users deviated from compliantly executing the template, comprises:

means for modifying the template by modifying one or more relationships between a plurality of emulatable aspects included in the template.

34. The computationally-implemented system of claim 33, wherein said means for modifying the template by modifying one or more relationships between a plurality of emulatable aspects included in the template, comprises:

means for modifying the template by modifying one or more temporal relationships between the plurality of emulatable aspects included in the template.

35. The computationally-implemented system of claim 33, wherein said means for modifying the template by modifying one or more relationships between a plurality of emulatable aspects included in the template, comprises:

means for modifying the template by modifying one or more specific time relationships between the plurality of emulatable aspects included in the template.

36. The computationally-implemented system of claim 1, wherein said means for modifying the template to include at least one plausible emulatable aspect that has been determined to have been successfully emulated by at least a portion of the plurality of end users, comprises:

means for modifying the template to include at least one plausible emulatable aspect that has been determined to have been successfully emulated by a majority of the plurality of end users.

37. The computationally-implemented system of claim 1, wherein said means for modifying the template based, at least in part, on determining that the plurality of end users deviated from compliantly executing the template, comprises:

means for modifying the template to include at least one emulatable aspect that was provided by at least analyzing a plurality of reported aspects of the plurality of end users, the plurality of reported aspects deviating from at least one of the one or more emulatable aspects included in the template.

38. The computationally-implemented system of claim 37, wherein said means for modifying the template to include at least one emulatable aspect that was provided by at least analyzing a plurality of reported aspects of the plurality of end users, the plurality of reported aspects deviating from at least one of the one or more emulatable aspects included in the template, comprises:
- means for modifying the template to include at least one mean value emulatable aspect that was at least provided by developing a mean value for a plurality of reported aspects of the plurality of end users, the reported aspects corresponding to and deviating from at least one of the one or more emulatable aspects included in the template.

39. The computationally-implemented system of claim 37, wherein said means for modifying the template to include at least one emulatable aspect that was provided by at least analyzing a plurality of reported aspects of the plurality of end users, the plurality of reported aspects deviating from at least one of the one or more emulatable aspects included in the template, comprises:
- means for modifying the template to include at least one average value emulatable aspect that was at least provided by developing an average value for a plurality of reported aspects of the plurality of end users, the plurality of reported aspects corresponding to and deviating from at least one of the one or more emulatable aspects included in the template.

40. The computationally-implemented system of claim 37, wherein said means for modifying the template to include at least one emulatable aspect that was provided by at least analyzing a plurality of reported aspects of the plurality of end users, the plurality of reported aspects deviating from at least one of the one or more emulatable aspects included in the template, comprises:
- means for modifying the template to include at least one emulatable aspect that was provided by determining from a plurality of reported aspects of the plurality of end users an end user aspect that was reported more than once, the plurality of reported aspects corresponding to and deviating from at least one of the one or more emulatable aspects included in the template.

41. The computationally-implemented system of claim 40, wherein said means for modifying the template to include at least one emulatable aspect that was provided by determining from a plurality of reported aspects of the plurality of end users an end user aspect that was reported more than once, the plurality of reported aspects corresponding to and deviating from at least one of the one or more emulatable aspects included in the template, comprises:
- means for modifying the template to include at least one emulatable aspect that was provided by determining a reported aspect that was most commonly reported aspect from a plurality of reported aspects of the plurality of end users, the plurality of reported aspects corresponding to and deviating from at least one of the one or more emulatable aspects included in the template.

42. The computationally-implemented system of claim 1, wherein said means for modifying the template based, at least in part, on determining that the plurality of end users deviated from compliantly executing the template, comprises:
- means for modifying the template based, at least in part, on determining that the plurality of end users deviated from the compliant execution of the template, the plurality of end users determined to have achieved the one or more target outcomes even though the template was not compliantly executed by the plurality of end users.

43. The computationally-implemented system of claim 1, further comprising:
- means for presenting the modified template.

44. A method for modifying one or more templates, comprising:
- determining, by electrical circuitry, whether a plurality of end users deviated from compliantly executing a template designed to facilitate the plurality of end users in achieving one or more target outcomes when one or more emulatable aspects included in the template are emulated by the plurality of end users, the one or more emulatable aspects being based on one or more relevant reported aspects of one or more source users that were deemed to have been relevant to achieving the one or more target outcomes; and
- modifying the template based, at least in part, on determining that the plurality of end users deviated from compliantly executing the template, wherein said modifying the template based, at least in part, on determining that the plurality of end users deviated from compliantly executing the template comprises:
  - modifying the template to include at least one plausible emulatable aspect that has been determined to have been successfully emulated by at least a portion of the plurality of end users.

45. A server, comprising:
- a deviation determining module configured to determine whether a plurality of end users deviated from compliantly executing a template designed to facilitate the plurality of end users in achieving one or more target outcomes when one or more emulatable aspects included in the template are emulated by the plurality of end users, the one or more emulatable aspects being based on one or more relevant reported aspects of one or more source users that were deemed to have been relevant to achieving the one or more target outcomes;
- a template modifying module configured to modify the template based, at least in part, on determining that the plurality of end users deviated from compliantly executing the template, wherein said template modifying module comprises:
  - a template modifying module configured to modify the template to include at least one plausible emulatable aspect that has been determined to have been successfully emulated by at least a portion of the plurality of end users; and
- one or more processors.

\* \* \* \* \*